(12) United States Patent
Bang-Andersen et al.

(10) Patent No.: US 6,890,916 B2
(45) Date of Patent: May 10, 2005

(54) INDOLE DERIVATIVES USEFUL FOR THE TREATMENT OF CNS DISORDERS

(75) Inventors: Benny Bang-Andersen, København S (DK); Jakob Felding, Charlottenlund (DK); Jan Kehler, Kgs. Lyngby (DK); Kim Andersen, Ridgewood, NJ (US)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 10/315,927

(22) Filed: Dec. 9, 2002

(65) Prior Publication Data

US 2003/0191133 A1 Oct. 9, 2003

Related U.S. Application Data

(63) Continuation of application No. PCT/DK01/00406, filed on Jun. 13, 2001.
(60) Provisional application No. 60/212,445, filed on Jun. 16, 2000.

(30) Foreign Application Priority Data

Jun. 14, 2000 (DK) ........................ 2000 00919

(51) Int. Cl.⁷ ..................... A61K 31/33; A61K 31/445; A61K 31/47; C07D 215/00; C07D 401/00
(52) U.S. Cl. .................. 514/183; 514/319; 514/415; 514/312; 546/153; 546/157; 546/198; 546/201
(58) Field of Search ................. 514/183, 319, 514/415, 312; 546/153, 157, 198, 201 469, 454, 452

(56) References Cited

FOREIGN PATENT DOCUMENTS

| EP | 1 106 605 | 6/2001 | ......... C07D/209/16 |
|---|---|---|---|
| WO | 93/16073 | 8/1993 | ......... C07D/417/12 |
| WO | 98/28293 | 7/1998 | ......... C07D/401/04 |
| WO | 99/11619 | 3/1999 | ......... C07D/209/16 |
| WO | 99/58525 | 11/1999 | ......... C07D/401/14 |
| WO | 31074 | * 6/2000 | |
| WO | 00/31074 | 6/2000 | ......... C07D/417/14 |
| WO | 00/40581 | 7/2000 | ......... C07D/413/14 |
| WO | 00/69424 | 11/2000 | .......... A61K/31/00 |

OTHER PUBLICATIONS

Chemical Abstract DN 133:17486, also cited as WO 31074.*
Saxena P.R. Pharm. Ther. vol. 66 pp339–68(1995).*
Cecil Textbook of Medicine, 2oth Edition, vol. 2, pp. 1992–1996(1996).*
Joseph T. Coyle, Science vol. 219,1184–90(1983).*

* cited by examiner

*Primary Examiner*—Richard L. Raymond
*Assistant Examiner*—Sudhaker B. Patel
(74) *Attorney, Agent, or Firm*—Darby & Darby

(57) ABSTRACT

The present invention relates to dopamine $D_4$ ligands having the general formula I

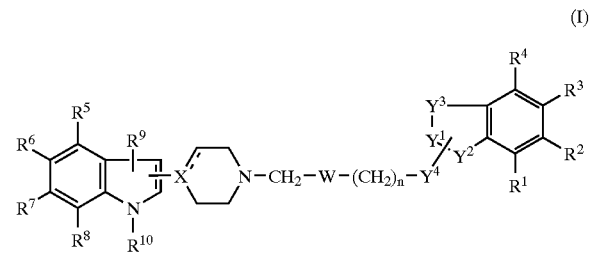

(I)

wherein $R^1$—$R^{10}$, W, X, $Y^1$—$Y^4$, and n are as described herein.

The compounds of the invention are potent dopamine $D_4$ receptor ligands.

26 Claims, No Drawings

INDOLE DERIVATIVES USEFUL FOR THE TREATMENT OF CNS DISORDERS

This application is a continuation of International application no. PCT/DK01/00406, filed Jun. 13, 2001, and claims priority under 35 U.S.C. §119 of U.S. provisional application Ser. No. 60/212,445, filed Jun. 16, 2000. The prior applications are hereby incorporated by reference, in their entirety.

FIELD OF THE INVENTION

The present invention relates to a novel class of indole derivatives having affinity for the dopamine $D_4$ receptor. The compounds have antagonistic effect at the dopamine $D_4$ receptor and are therefore useful in the treatment of certain psychiatric and neurologic disorders, in particular psychoses. Some of the compounds also have affinity for the dopamine $D_3$ receptor, the 5-$HT_{2A}$ receptor and/or the 5-$HT_{2C}$ receptor and some of the compounds are serotonin reuptake inhibitors.

BACKGROUND OF THE INVENTION

Dopamine $D_4$ ligands related to the compounds of the invention are known from WO 98/28293. The indane and dihydroindole derivatives disclosed therein have the general formula

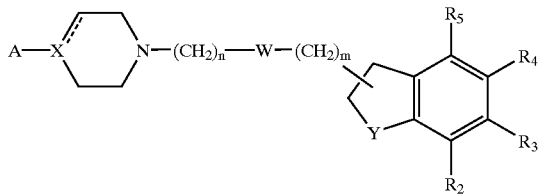

wherein A is an indole and Y is a group completing an indane, or a dihydroindole and the other substituents are as defined in the application.

WO 00/23441 discloses compounds of the general formula

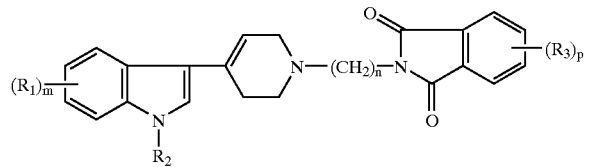

wherein the substituents $R_1$, $R_2$, $R_3$, m, n and p are as defined in the application. The compounds are said to show high affinity to dopamine $D_2$ receptors and are also said to be serotonin reuptake inhibitors. The compounds are claimed to be useful for the treatment of schizophrenia and other psychotic disorders.

Other compounds structurally related to the compounds of the invention are described in WO 99/58525. The compounds disclosed therein are said to be 5-$HT_{2A}$ ligands and serotonin reuptake inhibitors and have the general formula

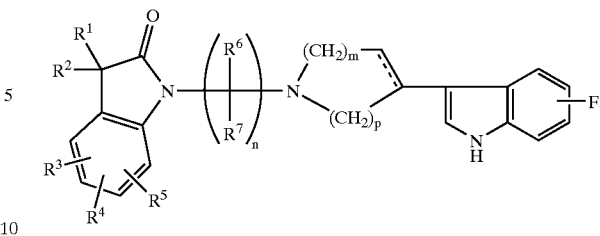

wherein the substituents are as defined in the application. The compounds are said to be useful for the treatment of schizophrenia.

WO 00/31074 relates to compounds having the formula

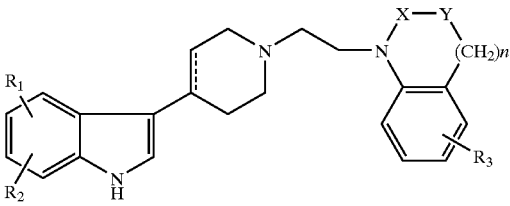

wherein X is CO or $SO_2$ and Y is N—$R^4$ or $CR^4R^5$ and the substitutents are as described in the application. The compounds are said to be active at the 5-$HT_{2A}$ receptor, to have 5-HT reuptake inhibiting activity and to enhance 5-HT release.

The applications, WO 94/18197, EP 329168, WO 93/16073, EP 732332, WO98/37893 and WO 95/11680, disclose dopamine $D_4$ ligands, which, like the compounds of the present invention, are substituted tetrahydroquinolinone and tetrahydroisoquinolinone derivatives. However, these compounds do not contain an indole as the compounds of the invention. The compounds are said to be dopamine $D_4$ ligands useful as antipsychotics. The compounds of WO 93/16073 are also claimed to have antagonistic activity at 5-$HT_2$ receptors.

Dopamine $D_4$ receptors belong to the dopamine $D_2$ subfamily of receptors, which is considered to be responsible for the antipsychotic effect of neuroleptics. The side effects of neuroleptic drugs, which primarily exert their effect via antagonism of $D_2$ receptors, are known to be due to $D_2$ receptor antagonism in the striatal regions of the brain. However, dopamine $D_4$ receptors are primarily located in areas of the brain other than striatum, suggesting that antagonists of the dopamine $D_4$ receptor will be devoid of extrapyramidal side effects. This is illustrated by the antipsychotic clozapine, which exerts higher affinity for $D_4$ than $D_2$ receptors, and is lacking extrapyramidal side effects (Van Tol et al. *Nature* 1991, 350, 610; Hadley *Medicinal Research Reviews* 1996, 16, 507–526 and Sanner *Exp. Opin. Ther. Patents* 1998, 8, 383–393).

A number of $D_4$ ligands, which were postulated to be selective $D_4$ receptor antagonists (L-745,879 and U-101958), have been shown to posses antipsychotic potential (Mansbach et al. *Psychopharmacology* 1998, 135, 194–200). However, recently it has been reported that these compounds are partial $D_4$ receptor agonists in various in vitro efficacy assays (Gazi et al. *Br. J. Pharmacol.* 1998, 124, 889–896 and Gazi et al. *Br. J. Pharmacol.* 1999, 128, 613–620). Furthermore, it was shown that clozapine, which is an effective antipsychotic, is a silent antagonist (Gazi et al. *Br. J. Pharmacol.* 1999, 128, 613–620).

Consequently, $D_4$ ligands, which are partial $D_4$ receptor agonists or antagonists, may have beneficial effects against psychoses.

Dopamine $D_4$ antagonists may also be useful for the treatment of cognitive deficits (Jentsch et al. *Psychopharmacology* 1999, 142, 78–84).

Further, evidence for a genetic association between the "primarily inattentive" subtype of ADHD and a tandem duplication polymorphism in the gene encoding the dopamine $D_4$ receptor has been published (McCracken et al. *Mol. Psychiat.* 2000, 5, 531–536). This clearly indicates a link between the dopamine $D_4$ receptor and ADHD, and ligands affecting this receptor may be useful for the treatment of this particular disorder Dopamine $D_3$ receptors also belong to the dopamine $D_2$ subfamily of receptors, and they are preferentially located in the limbic brain regions (Sokoloff et al. *Nature* 1990, 347, 146–151), such as the nucleus accumbens, where dopamine receptor blockade has been associated with antipsychotic activity (Willner *Int. Clinical Psychopharmacology* 1997, 12, 297–308). Furthermore, an elevation of the level of $D_3$ receptors in the limbic part of schizophrenic brains has been reported (Gurevich et al. *Arch Gen Psychiatry* 1997, 54, 225–32). Therefore, $D_3$ receptor antagonists may offer the potential for an effective antipsychotic therapy, free of the extrapyramidal side effects of the classical antipsychotic drugs, which primarily exert their effect by blockade of $D_2$ receptors (Shafer et al. *Psychopharmacology* 1998, 135, 1–16 and Schwartz et al. *Brain Research Reviews* 2000, 31, 277–287).

Moreover, $D_3$ receptor blockade results in a slight stimulation in the prefrontal cortex (Merchant et al. *Cerebral Cortex* 1996, 6, 561–570), which could be beneficial against negative symptoms and cognitive deficits associated with schizophrenia. In addition, $D_3$ antagonists can reverse $D_2$ antagonist-induced EPS (Millan et al. *Eur. J. Pharmacol.* 1997, 321, R7–R9) and do not cause changes in prolactin (Reavill et al. *J. Pharmacol. Exp. Ther.* 2000, 294, 1154–1165). Consequently, $D_3$ antagonistic properties of an antipsychotic drug could reduce the negative symptoms and cognitive deficits and result in an improved side effect profile with respect to EPS and hormonal changes.

Dopamine $D_3$ agonists have also been considered relevant in the treatment of schizophrenia (Wustow et al. *Current Pharmaceutical Design* 1997, 3, 391–404).

Various effects are known with respect to compounds, which are ligands at the different serotonin receptor subtypes. As regards the 5-$HT_{2A}$ receptor, which was previously referred to as the 5-$HT_2$ receptor, the following effects have been reported, e.g.:

Antidepressive effect and improvement of the sleep quality (Meert et al. Drug. Dev. Res. 1989, 18, 119), reduction of the negative symptoms of schizophrenia and of extrapyramidal side effects caused by treatment with classical neuroleptics in schizophrenic patients (Gelders *British J. Psychiatry* 1989, 155 (suppl. 5), 33). Furthermore, selective 5-$HT_{2A}$ antagonists could be effective in the prophylaxis and treatment of migraine (Scrip Report; "Migraine—Current trends in research and treatment"; PJB Publications Ltd.; May 1991) and in the treatment of anxiety (Colpart et al. *Psychopharmacology* 1985, 86, 303–305 and Perregaard et al. *Current Opinion in Therapeutic Patents* 1993, 1, 101–128).

Some clinical studies implicate the 5-$HT_2$ receptor subtype in aggressive behaviour. Further, atypical serotonin-dopamine antagonist neuroleptics have 5-$HT_2$ receptor antagonistic effect in addition to their dopamine blocking properties and have been reported to possess anti-aggressive behaviour (Connor et al. *Exp. Opin. Ther. Patents.* 1998, 8(4), 350–351).

Recently, evidence has also accumulated which support the rationale for selective 5-$HT_{2A}$ antagonists as drugs capable of treating positive symptoms of psychosis (Leysen et al. *Current Pharmaceutical Design* 1997, 3, 367–390 and Carlsson *Current Opinion in CPNS Investigational Drugs* 2000, 2(1), 22–24).

Compounds which are 5-HT reuptake inhibitors are well-known antidepressant drugs.

5-$HT_{2C}$ ligands have been found to augment the effect of 5-HT reuptake inhibitors in microdialysis experiments and animal models, and compounds having 5-HT reuptake inhibiting effect combined with affinity for the 5-$HT_{2C}$ receptor may therefore be particularly useful for the treatment of depression and other disorders responsive to serotonin reuptake inhibitors (PCT application No. PCT/DK00/00671).

Accordingly, dopamine $D_4$ receptor ligands are potential drugs for the treatment of schizophrenia and other psychoses, and compounds with combined effects at the 5-HT transporter may have the further benefit of improved effect on depressive and negative symptoms in schizophrenic patients. Compounds with combined effect at the dopamine $D_4$ receptor and the 5-$HT_{2A}$ receptor may have the benefit of improved effect on positive and negative symptoms of schizophrenia, and the benefit of effect on depressive and anxiety symptoms. Furthermore, dopamine $D_3$ antagonistic properties of an antipsychotic drug may reduce the negative symptoms and cognitive deficits of schizophrenia and result in an improved side effect profile.

SUMMARY OF THE INVENTION

The object of the present invention is to provide compounds that are partial agonists or antagonists at the dopamine $D_4$ receptor and such compounds with combined effects at the dopamine $D_4$ receptor, the $D_3$ receptor, the 5-$HT_{2A}$ receptor, the 5-$HT_{2C}$ receptor and/or the 5-HT transporter.

A further object of the present invention is to provide compounds with such activities which have improved solubility compared to prior art compounds.

Accordingly, the present invention relates to novel compounds of formula I

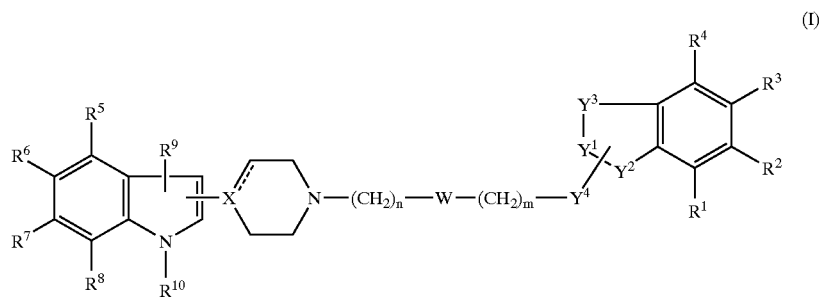

wherein
- (a) one of $Y^1$ and $Y^2$ is N, which is bound to $Y^4$, and the other of $Y^1$ and $Y^2$ is CO, CS, SO, or $SO_2$ and $Y^4$ is $CH_2$;
- (b) one of $Y^1$ and $Y^2$ is N, which is bound to $Y^4$, and the other of $Y^1$ and $Y^2$ is $CH_2$ and $Y^4$ is CO, CS, SO or $SO_2$; or
- (c) one of $Y^1$ and $Y^2$ is N, which is bound to $Y^4$, and the other of $Y^1$ and $Y^2$ is $CH_2$ and $Y^4$ is $CH_2$;

$Y^3$ is $Z\text{-}CH_2$, $CH_2\text{-}Z$ or $CH_2CH_2$, and Z is O or S; provided that when $Y^1$ is N, $Y^3$ may not be $Z\text{-}CH_2$;

W is a bond or an O, S, CO, CS, SO or $SO_2$ group;

n is 0–5, m is 0–5 and m+n is 1–10; provided that when W is O or S, then $n \geq 2$ and $m \geq 1$; when W is CO, CS, SO or $SO_2$, then $n \geq 1$ and $m \geq 1$;

X is C, CH or N; provided that when X is C, the dotted line indicates a bond, and when X is N or CH, the dotted line is not a bond;

$R^1$–$R^9$ are independently selected from hydrogen, halogen, cyano, nitro, amino, hydroxy, $C_{1-6}$-alkylamino, di-$C_{1-6}$-alkyl-amino, $C_{1-6}$-alkyl, $C_{2-6}$-alkenyl, $C_{2-6}$-alkynyl, $C_{1-6}$-alkoxy, $C_{1-6}$-alkylthio, $C_{1-6}$-alkyl substituted with hydroxy or thiol, $C_{3-8}$-cycloalkyl, $C_{3-8}$-cycloalkyl-$C_{1-6}$-alkyl, acyl, thioacyl, aryl, trifluoromethyl, trifluoromethylsulfonyl, and $C_{1-6}$ alkylsulfonyl;

$R^{10}$ is hydrogen, $C_{1-6}$-alkyl, $C_{2-6}$-alkenyl, $C_{2-6}$-alkynyl, $C_{1-6}$-alkyl substituted with hydroxy or thiol, $C_{3-8}$-cycloalkyl, $C_{3-8}$-cycloalkyl-$C_{1-6}$-alkyl, aryl, aryl-$C_{1-6}$-alkyl, acyl, thioacyl, $C_{1-6}$-alkylsulfonyl, trifluoromethylsulfonyl or arylsulfonyl or a pharmaceutically acceptable acid addition salt thereof.

In a first particular embodiment of the invention, the indole is bound to X via position 3 of the indole.

In a second embodiment of the invention, one of $Y^1$ and $Y^2$ is N which is bound to $Y^4$ and the other of $Y^1$ and $Y^2$ is CO, and $Y^4$ is $CH_2$.

In a third embodiment of the invention, one of $Y^1$ and $Y^2$ is N, which is bound to $Y^4$, and the other of $Y^1$ and $Y^2$ is $CH_2$ and $Y^4$ is CO.

In a fourth embodiment of the invention, $Y^1$ is a nitrogen bound to $Y^4$ and one of $Y^4$ and $Y^2$ is CO and the other is $CH_2$.

In a fifth embodiment of the invention, $Y^1$ is a nitrogen bound to $Y^4$, $Y^2$ is CO and $Y^4$ is $CH_2$.

In a sixth embodiment of the invention, $Y^1$ is a nitrogen bound to $Y^4$, $Y^2$ is $CH_2$ and $Y^4$ is CO.

In a seventh embodiment of the invention, $Y^2$ is a nitrogen bound to $Y^4$ and one of $Y^1$ and $Y^4$ is CO and the other is $CH_2$.

In an eighth embodiment of the invention, $Y^2$ is a nitrogen atom bound to $Y^4$, $Y^1$ is $CH_2$ and $Y^4$ is CO.

In a ninth embodiment of the invention, $Y^2$ is a nitrogen atom bound to $Y^4$, $Y^1$ is CO and $Y^4$ is $CH_2$.

In a tenth embodiment of the invention, one of $Y^1$ and $Y^2$ is N, which is bound to $Y^4$, and the other of $Y^1$ and $Y^2$ is $CH_2$ and $Y^4$ is $CH_2$. Such compounds are preferably in the form of pharmaceutically acceptable di-salts thereof.

In a further embodiment of the invention, $Y^3$ is $CH_2CH_2$ or $CH_2Z$.

In still further embodiments of the invention, X is C, X is N or X is CH.

The substituents $R^1$–$R^9$ are in particular selected from hydrogen, halogen, cyano, nitro, amino, $C_{1-6}$-alkylamino, di-$C_{1-6}$-alkylamino, $C_{1-6}$-alkyl, $C_{3-8}$-cycloalkyl and trifluoromethyl, and $R^{10}$ is hydrogen, $C_{1-6}$-alkyl or acyl and/or W is a bond and n+m is 1 to 6, in particular 3 to 6.

The compounds of the invention are partial agonists or antagonist at the dopamine $D_4$ receptor. Many compounds have combined effect at the dopamine $D_4$ receptor and dopamine $D_3$ receptor affinity, 5-$HT_{2A}$ receptor affinity, 5-$HT_{2C}$ receptor affinity and/or 5-HT reuptake inhibiting effect.

Accordingly, the compounds of the invention are considered useful in the treatment of positive and negative symptoms of schizophrenia, other psychoses, anxiety disorders, such as generalised anxiety disorder, panic disorder, and obsessive compulsive disorder, depression, aggression, side effects induced by conventional antipsychotic agents, migraine, cognitive disorders, ADHD and in the improvement of sleep.

In another aspect, the present invention provides a pharmaceutical composition comprising at least one compound of Formula I as defined above or a pharmaceutically acceptable acid addition salt thereof in a therapeutically effective amount and in combination with one or more pharmaceutically acceptable carriers or diluents.

In a further aspect, the present invention provides the use of a compound of Formula I as defined above or an acid addition salt thereof for the manufacture of a pharmaceutical preparation for the treatment of the above mentioned disorders.

DETAILED DESCRIPTION OF THE INVENTION

The compounds of general Formula I may exist as optical isomers thereof and such optical isomers are also embraced by the invention.

The term $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl, 2-methyl-1-propyl, pentyl and hexyl.

Similarly, $C_{2-6}$-alkenyl and $C_{2-6}$-alkynyl, respectively, designate such groups having from two to six carbon atoms, including one double bond and triple bond respectively, such as ethenyl, propenyl, butenyl, ethynyl, propynyl and butynyl.

The terms $C_{1-6}$-alkoxy, $C_{1-6}$-alkylthio, $C_{1-6}$-alkylsulfonyl, $C_{1-6}$-alkylamino, $C_{1-6}$-alkylcarbonyl, and the like, designate such groups in which the alkyl group is $C_{1-6}$ alkyl as defined above.

The term $C_{3-8}$-cycloalkyl designates a monocyclic or bicyclic carbocycle having three to eight C-atoms, such as cyclopropyl, cyclopentyl, cyclohexyl, etc.

The term aryl refers to a carbocyclic aromatic group, such as phenyl, naphthyl, in particular phenyl, including methyl substituted phenyl, or naphthyl.

Halogen means fluoro, chloro, bromo or iodo.

As used herein the term acyl refers to a formyl, $C_{1-6}$-alkylcarbonyl, arylcarbonyl, aryl-$C_{1-6}$-alkylcarbonyl, $C_{3-8}$-cycloalkylcarbonyl or a $C_{3-8}$-cycloalkyl-$C_{1-6}$-alkyl-carbonyl group and the term thioacyl is the corresponding acyl group in which the carbonyl group is replaced with a thiocarbonyl group.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients, or other additives normally used in the art may be used.

Conveniently, the compounds of the invention are administered in unit dosage form containing said compounds in an amount of about 0.01 to 100 mg.

The total daily dose is usually in the range of about 0.05–500 mg, and most preferably about 0.1 to 50 mg of the active compound of the invention.

The compounds of the invention may be prepared as follows:

1) Alkylating a piperazine, piperidine or tetrahydropyridine of formula II with an alkylating derivative of formula III:

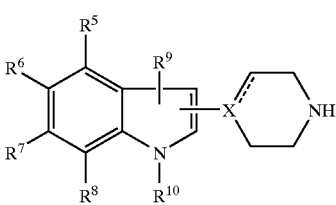

(II)

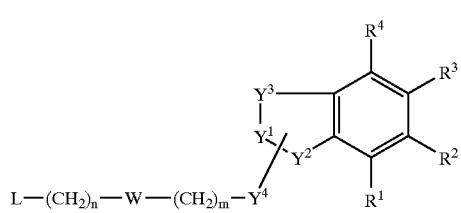

(III)

wherein $R^1$–$R^{10}$, X, $Y^1$, $Y^2$, $Y^3$, $Y^4$1 W, n, m and the dotted line are as previously defined, and L is a leaving group such as e.g. halogen, mesylate or tosylate;

2) Reductive alkylation of an amine of formula II with a reagent of formula IV:

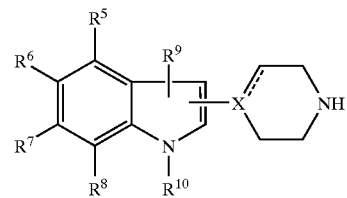

(II)

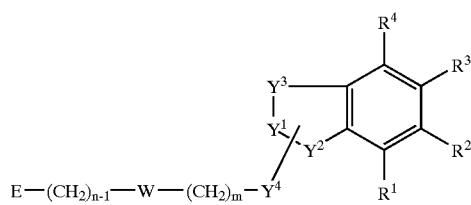

(IV)

wherein $R^1$–$R^{10}$, X, $Y^1$, $Y^2$, $Y^3$, $Y^4$, W, n, m and the dotted line are as previously defined and E is an aldehyde or an activated carboxylic acid group;

3) Alkylating a compound of formula V with an alkylating derivative of formula VI:

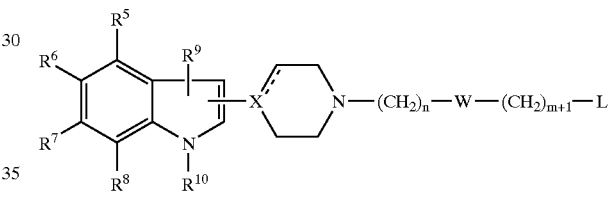

(VI)

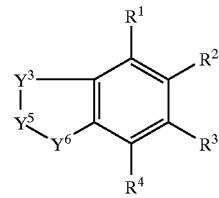

(V)

wherein $R^1$–$R^{10}$, X, $Y^3$, W, n, m and the dotted line are as previously defined, one of $Y^5$ and $Y^6$ is NH or $N^-$ and the other of $Y^5$ and $Y^6$ is CO, CS, SO, $SO_2$ or $CH_2$ and L is a leaving group such as e.g. halogen, mesylate or tosylate; or 4) Reducing the double bond in the tetrahydropyridinyl ring in derivatives of the following formula VII:

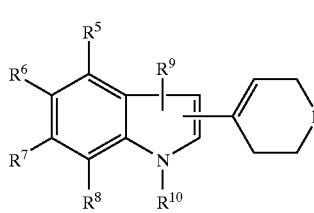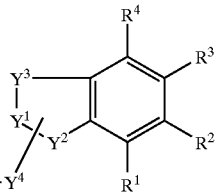

(VII)

wherein $R^1$–$R^{10}$, $Y^1$, $Y^2$, $Y^3$, $Y^4$, W, m and n are as previously defined;

5) Reducing the amide carbonyl in a compound of formula VIII:

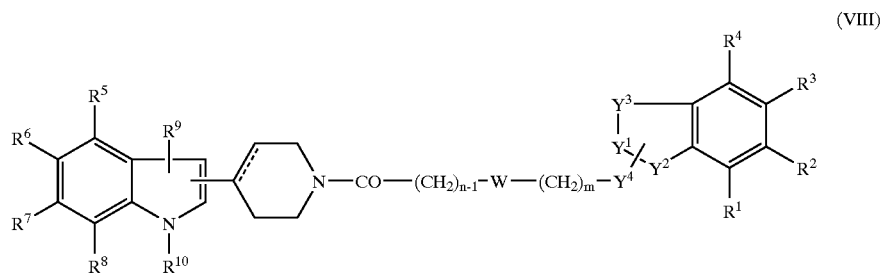

(VIII)

wherein $R^1$–$R^{10}$, $Y^1$, $Y^2$, $Y^3$, $Y^4$, n, m, W and the dotted line are as previously defined;

6) Reducing the amide group compounds of formula IX:

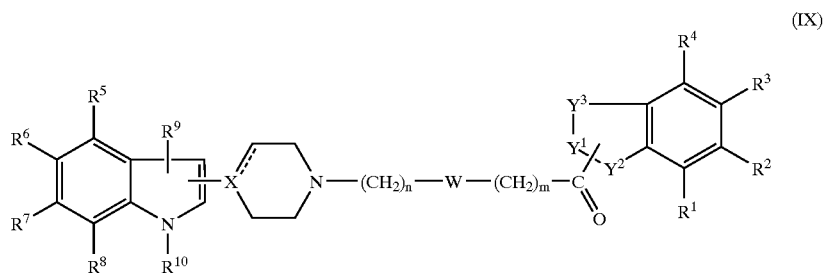

(IX)

wherein $R^1$–$R^{10}$, X, $Y^1$, $Y^2$, $Y^3$, n, m, W and the dotted line are as previously defined;

7) Reductive alkylation of a derivative of formula Va with an acylating derivative of formula X:

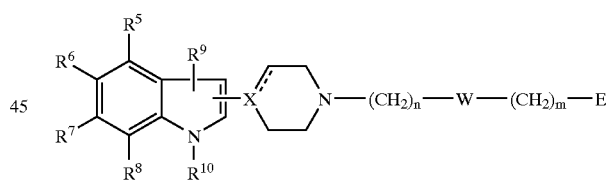

(X)

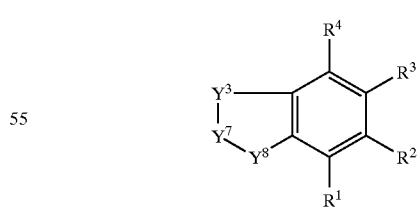

(Va)

wherein $R^1$–$R^{10}$, X, $Y^3$, W, n, m and the dotted line are as previously defined, one of $Y^7$ and $Y^8$ is NH and the other of $Y^7$ and $Y^8$ is $CH_2$ and E is an aldehyde or an activated carboxylic acid;

8) Acylation of an amine of formula Va with a reagent of formula X:

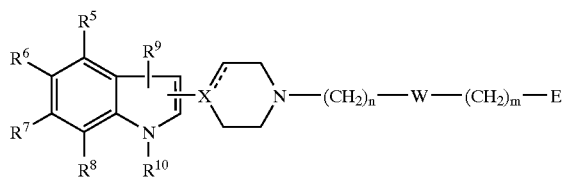

(X)

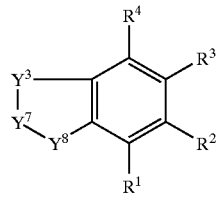

(Va)

wherein $R^1$–$R^{10}$, X, $Y^3$, W, n, m and the dotted line are as previously defined, one of $Y^7$ and $Y^8$ is NH and the other of $Y^7$ and $Y^8$ is $CH_2$ and E is an aldehyde or an activated carboxylic acid;

9) Cleaving a polymer bound derivative of formula XI

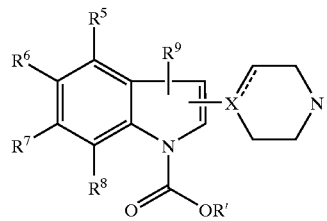 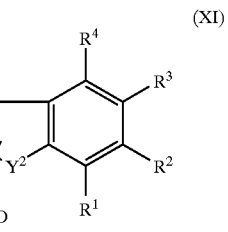

(XI)

wherein $R^1$–$R^9$, $Y^1$, $Y^2$, $Y^3$, X, W, m and n are as previously defined and R'OH is hydroxyethyl or hydroxymethyl polystyrene, Wang resin or analogous polyethylene glycol polystyrene resins; whereupon the compound of Formula I is isolated as the free base or a pharmaceutically acceptable acid addition salt thereof.

The alkylation according to method 1) and 3) is conveniently performed in an inert organic solvent such as a suitably boiling alcohol or ketone, preferably in the presence of an organic or inorganic base (potassium carbonate, diisopropylethylamine or triethylamine) at reflux temperature. Alternatively, the alkylation can be performed at a fixed temperature, which is different from the boiling point, in one of the above-mentioned solvents or in dimethyl formamide (DMF), dimethylsulfoxide (DMSO) or N-methylpyrrolidin-2-one (NMP), preferably in the presence of a base.

The synthesis the amines of formula (II), 3-(piperidin-4-yl)-1H-indoles and 3-(3,6-dihydro-2H-pyridin-4-yl)-1H-indoles has been described in the literature (see e.g. EP-A1-465398). Alkylating reagents of formula (III) are known from the literature (see Oshiro et al. *J. Med. Chem.* 2000, 43, 177–189 and EP-B1-512525), or they can be prepared by methods obvious to a chemist skilled in the art (see e.g. Kowalski et al. *J. Heterocyclic Chem.* 2000, 37, 187–189, Mokrosz et al. *Pharmazie* 1997, 52, 423–428 and Misztal et al. *Med. Chem. Res.* 1992, 2, 82–87). Alkylating reagents of formula (VI) can be prepared by methods obvious to a chemist skilled in the art, and amines of formula (V) are commercially available or described in the literature.

The reductive alkylation according to methods 2) and 7) is performed by standard literature methods. The reaction can be performed in two steps, e.g. coupling of derivatives of formula II/Va and the reagent of formula IV/X by standard methods via the carboxylic acid chloride or by use of coupling reagents such as e.g. dicyclohexyl carbodiimide followed by reduction of the resulting amide with lithium aluminium hydride or alane. The reaction can also be performed by a standard one-pot procedure. Carboxylic acids or aldehydes of formula IV/X can be prepared by methods obvious to a chemist skilled in the art.

The alkylation according to method 3) is conveniently performed as described above or by reacting the nitrogen anion of V with VI. The nitrogen anion of V can be prepared in an inert organic solvent, e.g. dimethyl formamide (DMF), dimethylsulfoxide (DMSO) or N-methylpyrrolidin-2-one (NMP), by the use of a strong base, e.g. NaH, before the alkylation.

The reduction of the double bond according to method 4) is generally performed by catalytic hydrogenation at low pressure (<3 atm.) in a Parr apparatus, or by using reducing agents such as diborane or hydroboric derivatives as produced in situ from $NaBH_4$ in trifluoroacetic acid in inert solvents such as tetrahydrofuran (THF), dioxane or diethyl ether. Starting materials of formula (VII) may be prepared by methods 1), 3), 7) and 8).

Reduction of amide groups according to methods 5) and 6) is most conveniently performed with lithium aluminium hydride or alane in an inert organic solvent such as e.g. tetrahydrofuran (THF) or diethylether from 0° C. to reflux temperature. Starting materials of formula (VIII) may be prepared by methods 2) and 3), whereas starting materials of formula (IX) may be prepared by methods 1), 7) and 8).

The coupling according to method 8) is conveniently performed by the use of coupling reagents such as e.g. dicyclohexyl carbodiimide.

The derivatives of structure (XI) is prepared by means of a solid phase synthesis sequence as outlined in Scheme 1 below. The first building block (XII), prepared by methods obvious to the chemist skilled in the art, is generally attached to the resin (polystyrene bound ethyl 4-nitrophenyl carbonate) using base e.g. N,N-dimethylaminopyridine and N,N-diisopropylethylamine at elevated temperature (e.g. 50–100° C.) in an aprotic solvent (e.g. DMF or DMSO) to yield (XIII). After deprotection of the amino group by trifluoroacetic acid (resin XIV), the second diversifying building block was introduced by alkylation. The alkylation was performed at elevated temperature (50–100° C.) in an aprotic solvent such as DMF, acetone or acetonitrile leading to resin (XV). After deprotection of the carboxylic acid ester by trifluoroacetic acid (resin XVI), the third diversifying building block of formula (Va) was introduced by standard amide forming reaction sequence, e.g. converting the carboxylic acid to the corresponding acid chloride using thionyl chloride at low temperature in dichloromethane, acetonitrile or DMF followed by treatment with an amine. The final product was cleaved from the resin using diluted sodium methoxide in a methanol/tetrahydrofuran mixture at ambient temperature.

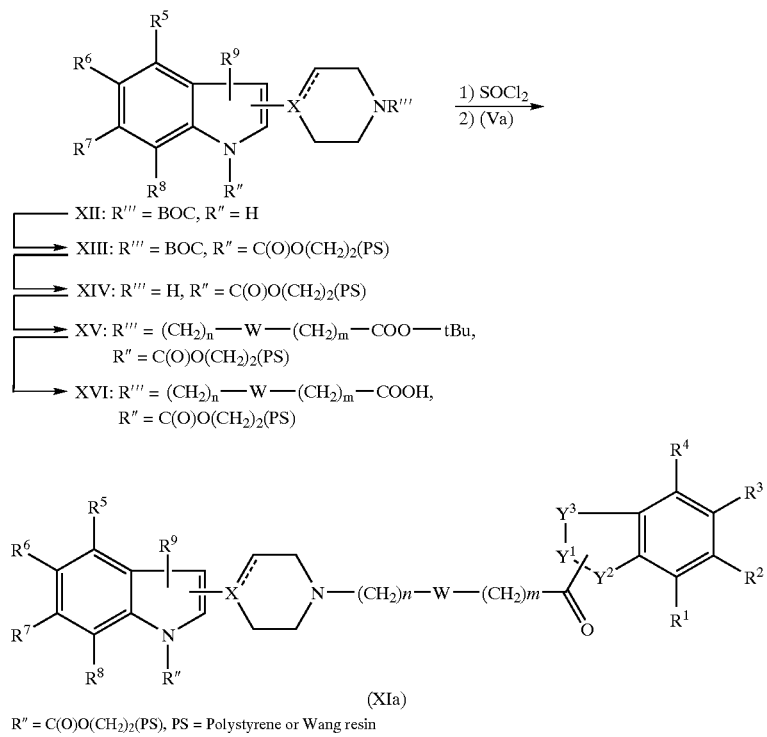

Experimental Section

Melting points were determined on a Büchi B-540 apparatus and are uncorrected. Mass spectra were obtained on a Quattro MS-MS system from VG Biotech, Fisons Instruments. Analytical LC-MS data were obtained on a PE Sciex API 150EX instrument equipped with IonSpray source and Shimadzu LC-8A/SLC-10A LC system. The LC conditions (50×4.6 mm YMC ODS-A with 5 µm particle size) were linear gradient elution with water/acetonitrile/trifluoroacetic acid (90:10:0.05) to water/acetonitrile/trifluoroacetic acid (10:90:0.03) in 7 min at 2 mL/min. Purity was determined by integration of the UV trace (254 nm). The retention times $R_t$ are expressed in minutes. Preparative LC-MS-separation was performed on the same instrument. The LC conditions (50×20 mm YMC ODS-A with 5 µm particle size) were linear gradient elution with water/acetonitrile/trifluoroacetic acid (80:20:0.05) to water/acetonitrile/trifluoroacetic acid (5:95:0.03) in 7 min at 22.7 mL/min. Fraction collection was performed by split-flow MS detection. $^1$H NMR spectra were recorded at 250.13 MHz on a Bruker AC 250 or at 500.13 MHz on a Bruker DRX 500. Deuterated chloroform (99.8% D) or dimethylsulfoxide (99.9% D) were used as solvents. TMS was used as internal reference standard. Chemical shifts are expressed as ppm values. The following abbreviations are used for multiplicity of NMR signals: s=singlet, d=doublet, t=triplet, q=quartet, qv=quintet, h=heptet, dd=double doublet, dt=double triplet, dq=double quartet, tt=triplet of triplets, m=multiplet, b=broad. NMR signals corresponding to acidic protons are to some extent omitted. Content of water in crystalline compounds was determined by Karl Fischer titration. For column chromatography, silica gel of type Kieselgel 60, 40–60 mesh ASTM was used. For ion-exchange chromatography, the following material was used: SCX-columns (1 g) from Varian Mega Bond Elut®, Chrompack cat. No. 220776. Prior to use, the SCX-columns were pre-conditioned with 10% solution of acetic acid in methanol (3 mL).

EXAMPLES

Preparation of Intermediates

A. Alkylating Reagents 1-(2-Chloroethyl)-3,4-dihydroquinolin-2(1H)-one

A suspension of sodium hydride (3.0 g, 60% in mineral oil) and dimethyl formamide (100 mL) was kept at 15–18° C. followed by the addition of a solution of 3,4-dihydroquinolin-2(1H)-one (10.0 g) in dimethyl formamide (150 mL). The resulting mixture was stirred at room temperature for 60 min followed by the addition of a solution of 2-chloroethyl acetate (10.0 g) in dimethyl formamide (50 mL) at a temperature of 20° C. The resulting mixture was heated at 80° C. for 2½ h, cooled and poured onto ice. The aqueous phase was extracted with ethyl acetate, and the combined organic phases were washed with brine, dried (MgSO$_4$) and concentrated in vacuo. The crude product was purified by flash chromatography on silicagel (eluent: ethyl acetate/heptane 1:1) to give crude 1-(2-acetoxyethyl)-3,4-dihydroquinolin-2(1H)-one (10.2 g). A mixture of crude 1-(2-acetoxyethyl)-3,4-dihydroquinolin-2(1H)-one, sodium methanolate (2.5 mL, 30% in methanol) and methanol (250 mL) was stirred at room temperature for 16 h and subsequently concentrated in vacuo. The residue was purified by flash chromatography on silicagel (eluent: ethyl acetate/heptane 1:1) to give the corresponding alcohol as a red crystalline compound (4.9 g). This alcohol was dissolved in tetrahydrofuran (100 mL) followed by the addition of triethylamine (8.2 mL). The resulting mixture was cooled to 5–6° C. followed by the addition of a solution of methane sulfonic acid chloride (2 mL) in tetrahydrofuran (25 mL). The mixture was filtered and evaporated to dryness in vacuo. The residue was dissolved in dimethyl formamide (50 mL) followed by addition of lithium chloride (4.9 g), and the resulting mixture was heated at 70° C. for 5 min. The mixture was poured onto brine, and the aqueous phase was extracted with ethyl acetate. The combined organic phases were dried (MgSO$_4$), filtered and concentrated in vacuo. The residue was purified by flash chromatography on silicagel (eluent:ethyl acetate/heptane 1:1) to give the product as a red oil (2.9 g).

1-(3-Bromopropan-1-yl)-3,4-dihydroquinolin-2(1H)-one

A suspension of sodium hydride (6.8 g, 60% in mineral oil) and dimethyl formamide (200 mL) was kept at 20–25° C. followed by the addition of a solution of 3,4-dihydroquinolin-2(1H)-one (25.0 g) in dimethyl formamide (180 mL). The resulting mixture was stirred at room temperature for 10 min followed by the addition of a solution of 1,3-dibromopropane (172 g) in dimethyl formamide (150 mL) at a temperature of 20–35° C. The resulting mixture was stirred at 30° C. for 20 min and concentrated in vacuo. The residue was poured onto ice, and the aqueous phase was extracted with ethyl acetate. The combined organic phases were washed with brine, dried (MgSO$_4$) and concentrated in vacuo. The crude product was purified by flash chromatography on silicagel (eluent:ethyl acetate/heptane 1:1) to give the product as a yellow oil (27 g).

The following compounds were prepared in a similar manner 1-(4-Bromobutan-1-yl)-3,4-dihydroquinolin-2(1H)-one
from 3,4-dihydroquinolin-2(1H)-one and 1,4-dibromobutane 1-(5-Bromopentan-1-yl)-3,4-dihydroquinolin-2(1H)-one
from 3,4-dihydroquinolin-2(1H)-one and 1,5-dibromopentane 4-(4-Bromobutan-1-yl)-3,4-dihydro-2H-1,4-benzoxazin-3(4H)-one
from 3,4-dihydro-2H-1,4-benzoxazin-3(4H)-one and 1,4-dibromobutane 2-(3-Hydroxypropan-1-yl)-3,4-dihydroisoquinolin-1(2H)-one
from 3,4-dihydroisoquinolin-1(2H)-one and 3-bromopropanol 2-(4-Bromobutan-1-yl)-3,4-dihydroisoquinolin-1(2H)-one
from 3,4-dihydroisoquinolin-1(2H)-one and 1,4-dibromobutane 1-(3-Bromopropan-1-yl)-3,4-dihydroisoquinolin-1(2H)-one The compound 2-(3-hydroxypropan-1-yl)-3,4-dihydroisoquinolin-1(2H)-one was dissolved in tetrahydrofuran (100 mL) followed by the addition of triethylamine (5.2 mL). The resulting mixture was cooled to 6–11° C. followed by the addition of a solution of methane sulfonic acid chloride (1.4 mL) in tetrahydrofuran (25 mL). The mixture was stirred at 5° C. for 10 min, filtered and concentrated in vacuo. The residue was dissolved in acetone (250 mL) followed by addition of lithium bromide (6.5 g), and the resulting mixture was boiled under reflux for 2 h. The mixture was poured onto brine, and the aqueous phase was extracted with ethyl acetate. The combined organic phases were dried (MgSO$_4$), filtered and concentrated in vacuo. The residue was purified by flash chromatography on silicagel (eluent:ethyl acetate/heptane 1:2) to give the product as a yellow oil (2.7 g).

3-Chloro-1-(3,4-dihydro-1H-isoquinolin-2-yl)propan-1-one

A solution of 3-chloropropanoyl chloride (10.5 g) in tetrahydrofuran (400 mL) was cooled down to 6° C. followed by the addition of a solution of 3,4-dihydro-1H-isoquinoline (10.0 g). The resulting mixture was stirred at 10° C. for 30 min, filtered and concentrated in vacuo. The residue was subjected to a standard aqueous work up procedure followed by purification by flash chromatography on silicagel (eluent:ethyl acetate/heptane 1:1) to give the product as a colourless oil (10 g).

The following compounds were prepared in a similar manner

3-Bromo-1-(3,4-dihydro-1H-isoquinolin-2-yl)propan-1-one
from 3,4-dihydro-1H-isoquinoline and 3-bromopropanoyl chloride 4-Chloro-1-(3,4-dihydro-1H-isoquinolin-2-yl)butan-1-one
from 3,4-dihydro-1H-isoquinoline and 4-chlorobutanoyl chloride 4-Chloro-1-(3,4-dihydro-2H-quinolin-1-yl)butan-1-one
from 3,4-dihydro-2H-quinoline and 4-chlorobutanoyl chloride Preparation of Solid Supported Intermediates Preparation of 4-nitrophenyloxycarbonyloxyethyl polystyrene A 2 L round bottom flask was charged with hydroxyethyl polystyrene (62.9 g, 83 mmol, commercially available from Rapp Polymere, cat. no. HA 1 400 00), N-methylmorpholine (20 mL, 183 mmol) and dry dichloromethane (900 mL). The suspension was cooled on an ice bath and 4-nitrophenyl chloroformate dissolved in dry dichloromethane (400 mL) was added during 5 minutes. The mixture was stirred at room temperature for 16 h. The resin was filtered off and washed with dry dichloromethane (5×200 mL). The resin was dried in vacuo (20° C., 72 h) to yield the title resin (79.6 g).

Preparation of Polymer Bound 7-chloro-3-(piperidin-4-yl)-1H-indole

A 100 mL round bottom flask was charged with 4-nitrophenyloxycarbonyloxyethyl polystyrene (4.0 g, 4.3 mmol), 7-chloro-3-(1-tert-butoxycarbonylpiperidin-4-yl)-1H-indole (2.7 g, 8.1 mmol), diisopropylethylamine (3.5 mL, 20.2 mmol), 4-dimethylaminopyridine (0.5 g, 4 mmol) and dry dimethyl formamide (50 mL). The mixture was stirred at 90° C. for 72 h. After cooling to room temperature, the resin was filtered off and washed with dry dimethyl formamide (3×25 mL), dry acetonitrile (3×25 mL) and dry dichloromethane (3×25 mL). The resin was transferred to a 250 mL glass cylinder with a fritte and a three way junction in the bottom. The resin was then treated for 20 minutes with 60 mL of a 1:1 mixture of dichloromethane and trifluoroacetic acid containing anisole (2%, w/w) and methionine (0.2 %, w/w), using a flow of nitrogen to agitate the resin (Caution: Generation of carbon dioxide). The resin was filtered off and washed with dry dichloromethane (25 mL), a 1:1 mixture of dichloromethane:triethylamine (3×25 mL) and dry dichloromethane (3×25 mL). The resin was dried in vacuo (20° C., 20 h) to yield the title resin (3.8 g).

The following polymer bound compounds were prepared in a similar manner

4-Chloro-3-(piperidin-4-yl)-1H-indole
4-Fluoro-3-(piperidin-4-yl)-1H-indole
5-Chloro-3-(piperidin-4-yl)-1H-indole
5-Fluoro-3-(piperidin-4-yl)-1H-indole
6-Chloro-3-(piperidin-4-yl)-1H-indole Preparation of Polymer Bound 3-[4-(7-chloro-1H-indol-3-yl)piperidin-1-yl]propionic acid A 25 mL round bottom flask was charged with polymer bound 7-chloro-3-(piperidin-4-yl)-1H-indole (1.0 g, 0.98 mmol), triethylamine (80.2 mL), tert-butyl 3-bromopropionate and dry acetonitrile (5 mL). The mixture was stirred at 80° C. for 3 h. After cooling to room temperature, the resin was filtered off and washed with dry acetonitrile (3×10 mL) and dry dichloromethane (3×10 mL). The resin was treated for 20 minutes with 8 mL of a 1:1 mixture of dichloromethane and trifluoroacetic acid containing anisole (2%, w/w) and methionine (0.2%, w/w) (Caution: Generation of carbon dioxide). The resin was filtered off and washed with dry dichloromethane (10 mL), a 1:1 mixture of dichloromethane:triethylamine (3×10 mL) and dry dichloromethane (3×10 mL). The resin was dried in vacuo (20° C., 20 h) to yield the title resin (1.0 g).

The following polymer bound compounds were prepared in a similar manner
3-[4-(4-Chloro-1H-indol-3-yl)piperidin-1-yl]propionic acid
3-[4-(4-Fluoro-1H-indol-3-yl)piperidin-1-yl]propionic acid
3-[4-(5-Fluoro-1H-indol-3-yl)piperidin-1-yl]propionic acid
3-[4-(6-Chloro-1H-indol-3-yl)piperidin-1-yl]propionic acid
4-[4-(4-Chloro-1H-indol-3-yl)piperidin-1-yl]butyric acid
4-[4-(4-Fluoro-1H-indol-3-yl)piperidin-1-yl]butyric acid
4-[4-(5-Chloro-1H-indol-3-yl)piperidin-1-yl]butyric acid
4-[4-(5-Fluoro-1H-indol-3-yl)piperidin-1-yl]butyric acid
4-[4-(7-Chloro-1H-indol-3-yl)piperidin-1-yl]butyric acid
5-[4-(4-Chloro-1H-indol-3-yl)piperidin-1-yl]pentanoic acid
5-[4-(5-Fluoro-1H-indol-3-yl)piperidin-1-yl]pentanoic acid
5-[4-(7-Chloro-1H-indol-3-yl)piperidin-1-yl]pentanoic acid
6-[4-(4-Fluoro-1H-indol-3-yl)piperidin-1-yl]hexanoic acid
6-[4-(4-Chloro-1H-indol-3-yl)piperidin-1-yl]hexanoic acid
6-[4-(5-Fluoro-1H-indol-3-yl)piperidin-1-yl]hexanoic acid
6-[4-(6-Chloro-1H-indol-3-yl)piperidin-1-yl]hexanoic acid
6-[4-(7-Chloro-1H-indol-3-yl)piperidin-1-yl]hexanoic acid Preparation of the Compounds of the Invention Example 1

1a, 5-Fluoro-3-{1-[2-(2-oxo-3,4-dihydro-2H-quinolin-1-yl)ethyl]piperidin-4-yl}-1H-indole hydrochloride A mixture of 5-fluoro-3-(piperidin-4-yl)-1H-indole (0.3 g), 1-(2-chloroethyl)-3,4-dihydroquinolin-2(1H)-one (0.41 g) and triethylamine (0.75 g) in dimethyl formamide (5 mL) and butanone (10 mL) was boiled under reflux for 6 h. The mixture was concentrated in vacuo, and the residue was purified by flash chromatography on silicagel (eluent:ethyl acetate/ethanol/triethylamine 90:10:5) to give the crude product, which was isolated as the hydrochloride salt from acetone as a white crystalline compound (0.04 g). $^1$H NMR (DMSO-$d_6$): 2.00–2.25 (m, 4H); 2.60 (t, 2H); 2.90 (t, 2H); 2.95–3.10 (m, 1H); 3.10–3.30 (m, 4H); 3.70 (d, 2H); 4.35 (t, 2H); 6.90 (t, 1H); 7.05 (t, 1H); 7.15–7.40 (m, 5H); 7.50 (d, 1H); 10.95 (broad s, 1H); 11.05 (s, 1H). MS m/z: 392 (MH+), 174.

The following compounds were prepared in a similar manner 1b, 5-Fluoro-3-{1-[3-(1-oxo-3,4-dihydro-1H-quinolin-2-yl)propan-1-yl]piperidin-4-yl}-1H-indole, oxalate from 5-fluoro-3-(piperidin-4-yl)-1H-indole and 1-(3-bromopropan-1-yl)-3,4-dihydroisoquinolin-1(2H)-one. $^1$H NMR (DMSO-$d_6$): 1.90–2.15 (m, 6H); 2.95–3.15 (m, 7H); 3.55–3.60 (m, 6H); 6.90 (t, 1H); 7.20 (s, 1H); 7.30 (d, 1H); 7.30–7.40 (m, 4H); 7.45–7.50 (m, 1H); 7.90 (d, 1H); 11.05 (s, 1H). MS m/z: 406 (MH+), 188.

1c, 5-Fluoro-3-{1-[4-(1-oxo-3,4-dihydro-1H-quinolin-2-yl)butan-1-yl]piperidin-4-yl}-1H-indole, hydrochloride from 5-fluoro-3-(piperidin-4-yl)-1H-indole and 2-(4-bromobutan-1-yl)-3,4-dihydroisoquinolin-1(2H)-one. $^1$H NMR (DMSO-$d_6$): 1.55–1.70 (m, 2H); 1.70–1.85 (m, 2H); 2.05 (d, 2H); 2.10–2.25 (m, 2H); 2.90 (t, 2H); 3.40–3.65 (m, 6H); 6.90 (t, 1H); 7.20 (s, 1H); 7.30 (d, 1H); 7.30–7.40 (m, 2H); 7.40–7.55 (m, 2H); 7.90 (d, 1H); 10.75 (broad s, 1H); 11.05 (s, 1H). MS m/z: 420 (MH+).

Example 2

2a, 5-Fluoro-3-{1-[3-(2-oxo-3,4-dihydro-2H-quinolin-1-yl)propan-1-yl]piperidin-4-yl}-1H-indole, hydrochloride A mixture of 5-fluoro-3-(piperidin-4-yl)-1H-indole (5.0 g), 1-(3-bromopropan-1-yl)-3,4-dihydroquinolin-2(1H)-one (7.7 g) and potassium carbonate (7.0 g) in dimethyl formamide (40 mL) was heated at 100° C. for 2½ h. The mixture was cooled, filtered and concentrated in vacuo. The residue was purified by flash chromatography on silicagel (eluent:ethyl acetate followed by ethyl acetate/ethanol 90:10) to give the product as an orange oil (9.1 g). The title compound (1.8 g of free base) was isolated as the hydrochloride salt from tetrahydrofuran as a white crystalline compound (1.5 g). Mp 210–212° C. $^1$H NMR (DMSO-$d_6$): 2.00–2.20 (m, 6H); 2.60 (t, 2H); 2.90 (t, 2H); 2.95–3.10 (m, 3H); 3.10–3.20 (m, 2H); 3.55 (d, 2H); 3.95 (t, 2H); 6.90 (t, 1H); 7.05 (t, 1H); 7.15–7.30 (m, 4H); 7.30–7.40 (m, 1H); 7.50 (d, 1H); 10.55 (broad s, 1H); 11.05 (s, 1H). MS m/z: 406 (MH+).

The following compounds were prepared in a similar manner 2b, 5-Fluoro-3-{1-[5-(2-oxo-3,4-dihydro-2H-quinolin-1-yl)pentan-1-yl]piperidin-4-yl}-1H-indole, hydrochloride from 5-fluoro-3-(piperidin-4-yl)-1H-indole and 1-(5-bromopentan-1-yl)-3,4-dihydroquinolin-2(1H)-one. Mp 199–200° C. $^1$H NMR (DMSO-$d_6$): 1.30–1.40 (m, 2H); 1.55–1.60 (m, 2H); 1.70–1.80 (m, 2H); 2.05–2.15 (m, 4H); 2.55 (t, 2H); 2.85 (t, 2H); 2.95–3.10 (m, 5H); 3.55 (d, 2H); 3.90 (t, 2H); 6.90 (t, 1H); 7.00 (t, 1H); 7.15 (d, 1H); 7.20–7.30 (m, 3H); 7.30–7.35 (m, 1H); 7.50 (d, 1H); 12.20 (broad s, 1H); 11.05 (s, 1H). MS m/z: 434 (MH+).

2c, 5-Chloro-3-{1-[3-(2-oxo-3,4-dihydro-2H-quinolin-1-yl)propan-1-yl]piperidin-4-yl}-1H-indole, hydrochloride from 5-chloro-3-(piperidin-4-yl)-1H-indole and 1-(3-bromopropan-1-yl)-3,4-dihydroquinolin-2(1H)-one. Mp 142–146° C. $^1$H NMR (DMSO-$d_6$): 1.95–2.15 (m, 6H); 2.60 (t, 2H); 2.90 (t, 2H); 2.95–3.15 (3H); 3.15–3.20 (m, 2H); 3.55 (d, 2H); 3.95 (t, 2H); 7.00–7.10 (m, 2H); 7.20–7.30 (m, 4H); 7.35 (d, 1H); 7.75 (s, 1H), 11.30 (broad, 1H); 11.15 (s, 1H). MS m/z: 422 (MH+), 188.

2d, 5-Chloro-3-{1-[4-(2-oxo-3,4-dihydro-2H-quinolin-1-yl)butan-1-yl]piperidin-4-yl}-1H-indole, hydrochloride from 5-chloro-3-(piperidin-4-yl)-1H-indole and 1-(4-bromobutan-1-yl)-3,4-dihydroquinolin-2(1H)-one. Mp 229–231° C. $^1$H NMR (DMSO-$d_6$): 1.55–1.65 (m, 2H); 1.70–1.80 (m, 2H); 2.00–2.15 (m, 4H); 2.55 (t, 2H); 2.85 (t, 2H); 2.95–3.15 (m, 5H); 2.55 (d, 2H); 3.95 (t, 2H); 7.00 (t, 1H); 7.05 (d, 1H); 7.15 (d, 1H); 7.20–7.30 (m, 3H); 7.40 (d, 1H); 7.75 (s, 1H); 10.05 (broad s, 1H); 11.10 (s, 1H). MS m/z: 436 (MH+).

2e, 5-Chloro-3-{1-[5-(2-oxo-3,4-dihydro-2H-quinolin-1-yl)pentan-1-yl]piperidin-4-yl}-1H-indole, hydrochloride from 5-chloro-3-(piperidin-4-yl)-1H-indole and 1-(5-bromopentan-1-yl)-3,4-dihydroquinolin-2(1H)-one. Mp 206–209° C. $^1$H NMR (DMSO-$d_6$): 1.30–1.40 (m, 2H); 1.55–1.65 (m, 2H); 1.70–1.80 (m, 2H); 2.00–2.15 (m, 4H); 2.55 (t, 2H); 2.85 (t, 2H); 2.95–3.10 (m, 4H); 3.10–3.25 (m, 1H); 3.55 (d, 2H); 3.90 (t, 2H); 7.00 (t, 1H); 7.05 (d, 1H); 7.15 (d, 1H); 7.20–7.30 (m, 3H); 7.40 (d, 1H); 7.75 (s, 1H); 11.20 (broad s, 1H); 11.15 (s, 1H). MS m/z: 450 (MH+), 299.

2f, 7-Chloro-3-{1-[4-(2-oxo-3,4-dihydro-2H-quinolin-1-yl)butan-1-yl]piperidin-4-yl}-1H-indole, hydrochloride from 7-chloro-3-(piperidin-4-yl)-1H-indole and 1-(4-bromobutan-1-yl)-3,4-dihydroquinolin-2(1H)-one. Mp 253–254° C. ¹H NMR (DMSO-d$_6$): 1.55–1.65 (m, 2H); 1.75–1.85 (m, 2H); 2.05–2.25 (m, 4H); 2.55 (t, 2H); 2.90 (t, 2H); 2.95–3.15 (m, 5H); 3.55 (d, 2H); 3.95 (t, 2H); 6.95–7.05 (m, 2H); 7.15–7.30 (m, 5H); 7.70 (d, 1H); 10.60 (broad s, 1H); 11.30 (s, 1H). MS m/z: 436 (MH+), 289.

2g, 5-Fluoro-3-{1-[4-(3-oxo-3,4-dihydro-2H-1,4-benzoxazin-4-yl)butan-1-yl]piperidin-4-yl}-1H-indole, hydrochloride from 5-fluoro-3-(piperidin-4-yl)-1H-indole and 4-(4-bromobutan-1-yl)-3,4-dihydro-2H-1,4-benzoxazin-3(4H)-one. Mp 83–92° C. ¹H NMR (DMSO-d$_6$): 1.60–1.70 (m, 2H); 1.75–1.85 (m, 2H); 2.00–2.20 (m, 4H); 2.95–3.15 (m, 5H); 3.55 (t, 2H); 4.65 (s, 2H); 6.90 (t, 1H); 7.00–7.05 (m, 2H); 7.05–7.15 (m, 1H); 7.20 (s, 1H); 7.25 (d, 1H); 7.30–7.40 (m, 1H); 7.50 (d, 1H); 10.45 (broad s, 1H); 11.05 (s, 1H). MS m/z: 422 (MH+), 273.

2h, 5-Chloro-3-{1-[4-(3-oxo-3,4-dihydro-2H-1,4-benzoxazin-4-yl)butan-1-yl]piperidin-4-yl}-1H-indole, hydrochloride from 5-chloro-3-(piperidin-4-yl)-1H-indole and 4-(4-bromobutan-1-yl)-3,4-dihydro-2H-1,4-benzoxazin-3(4H)-one. Mp 222–224° C. ¹H NMR (DMSO-d$_6$): 1.60–1.70 (m, 2H); 1.75–1.85 (m, 2H); 2.05–2.15 (m, 4H); 3.00–3.15 (m, 5H); 3.55 (d, 2H); 3.95 (t, 2H); 4.65 (s, 2H); 7.00–7.10 (m, 4H); 7.20 (s, 1H); 7.25 (d, 1H); 7.40 (d, 1H); 7.75 (s, 1H); 10.30 (broad s, 1H); 11.15 (s, 1H). MS m/z: 438 (MH+), 291, 204.

Example 3

3a, 5-Fluoro-3-{1-[3-(2-oxo-3,4-dihydro-2H-quinolin-1-yl)propan-1-yl]-3,6-dihydro-2H-pyridin-4-yl}-1H-indole, oxalate A mixture of 5-fluoro-3-(3,6-dihydro-2H-pyridin-4-yl)-1H-indole (3.0 g) and potassium carbonate (6.2 g) in butanone (250 mL) was heated until reflux temperature followed by the addition of 1-(3-bromopropan-1-yl)-3,4-dihydroquinolin-2(1H)-one (5.0 g) in butanone (50 mL). The resulting mixture was boiled under reflux for 10 h, filtered and concentrated in vacuo (7.7 g). The residue was purified by flash chromatography on silicagel (eluent:ethyl acetate/triethylamine 100:5) to give the crude product, which was crystallized from tetrahydrofuran/ethyl acetate. The title compound was isolated as the oxalate salt from acetone/tetrahydrofuran as a yellowish crystalline compound (1.7 g). Mp 203–206° C. ¹H NMR (DMSO-d$_6$): 1.95–2.05 (m, 2H); 2.55 (t, 2H); 2.75 (s, 2H); 2.85 (t, 2H); 3.15 (t, 2H); 3.35 (s, 2H); 3.80 (s, 2H); 3.95 (t, 2H); 6.05 (s, 1H); 6.95–7.05 (m, 2H); 7.15–7.30 (m, 3 H); 7.35–7.45 (m, 1H); 7.50–7.60 (m, 2H); 11.50 (s, 1H). MS m/z: 404 (MH+), 218.

The following compounds were prepared in a similar manner 3b, 5-Fluoro-3-{1-[4-(2-oxo-3,4-dihydro-2H-quinolin-1-yl)butan-1-yl]-3,6-dihydro-2H-pyridin-4-yl}-1H-indole, hydrochloride from 5-fluoro-3-(3,6-dihydro-2H-pyridin-4-yl)-1H-indole and 1-(4-bromobutan-1-yl)-3,4-dihydroquinolin-2(1H)-one. Mp 124–125° C. ¹H NMR (DMSO-d$_6$): 1.55–1.65 (m, 2H); 1.80 (q, 2H); 2.55 (t, 2H); 2.75 (d, 1H); 2.85–2.95 (m, 3H); 3.15–3.30 (m, 3H); 3.55–3.65 (m, 1H); 3.75 (d, 1H); 3.90–4.00 (m, 3H); 6.10 (s, 1H); 6.95–7.05 (m, 2H); 7.15 (d, 1H); 7.20–7.30 (m, 2H); 7.40–7.45 (m, 1H); 7.55–7.65 (m, 2H); 10.70 (broad s, 1H); 11.50 (s, 1H). MS m/z: 418 (MH+), 231.

3c, 5-Fluoro-3-{1-[5-(2-oxo-3,4-dihydro-2H-quinolin-1-yl)pentan-1-yl]-3,6-dihydro-2H-pyridin-4-yl}-1H-indole, oxalate from 5-fluoro-3-(3,6-dihydro-2H-pyridin-4-yl)-1H-indole and 1-(5-bromopentan-1-yl)-3,4-dihydroquinolin-2(1H)-one. Mp 205–207° C. ¹H NMR (DMSO-d$_6$): 1.35 (t, 2H); 1.55 (t, 2H); 1.75 (t, 2H); 2.55 (t, 2H); 2.75 (s, 2H); 2.85 (t, 2H); 3.10 (t, 2H); 3.35 (s, 2H); 3.80 (s, 2H); 3.90 (t, 2H); 6.10 (s, 1H); 6.95–7.05 (m, 2H); 7.15 (d, 1H); 7.20–7.30 (m, 2H); 7.40–7.45 (m, 1H); 7.55–7.60 (m, 2H); 11.50 (s, 1H). MS m/z: 432 (MH+), 245.

Example 4

4, 5-Fluoro-3-{1-[4-(2-oxo-3,4-dihydro-2H-quinolin-1-yl)butan-1-yl]piperidin-4-yl}-1H-indole, hydrochloride A mixture of 5-fluoro-3-{1-[4-(2-oxo-3,4-dihydro-2H-quinolin-1-yl)butan-1-yl]-3,6-dihydro-2H-pyridin-4-yl}-1H-indole (3.5 g), ethanol (100 mL), acetic acid (100 mL) and platinum oxide (0.4 g) was shaken under 3 atm for 16 h. The mixture was filtered, evaporated in vacuo to about a 100 mL, which subsequently was poured onto ice and added aqueous ammonia to basic pH. The aqueous phase was extracted with ethyl acetate, and the combined organic phases were washed with brine, dried (MgSO$_4$), and concentrated in vacuo. The residue was purified by flash chromatography on silicagel (eluent:ethyl acetate/triethylamine 100:4) to give the crude product (2.0 g). The title compound was isolated as the hydrochloride salt from ethyl acetate as a white crystalline compound (2.0 g). Mp 212–213° C. ¹H NMR (DMSO-d$_6$): 1.55–1.65 (m, 2H); 1.75–1.85 (m, 2H); 2.00–2.20 (m, 4H); 2.55 (t, 2H); 2.85 (t, 2H); 2.95–3.15 (m, 5H); 3.55 (d, 2H); 3.95 (t, 2H); 6.90 (t, 1H); 7.00 (t, 1H); 7.15–7.30 (m, 4H); 7.30–7.40 (m, 1H); 7.50 (d, 1H); 10.55 (broad s, 1H); 11.05 (s, 1H). MS m/z: 420 (MH+), 273, 202.

Example 5

5a, 5-Fluoro-1-methyl-3-{1-[3-(2-oxo-3,4-dihydro-2H-quinolin-1-yl)propan-1-yl]piperidin-4-yl}-1H-indole, oxalate A suspension of sodium hydride (0.5 g, 60% in mineral oil) and dimethyl formamide (60 mL) was kept at 22–24° C. followed by the addition of a solution of 5-fluoro-3-{1-[3-(2-oxo-3,4-dihydro-2H-quinolin-1-yl)propan-1-yl]piperidin-4-yl}-1H-indole (4.9 g) in dimethyl formamide (50 mL). The resulting mixture was stirred at room temperature for 25 min followed by the addition of a solution of methyl iodide (2.0 g) in dimethyl formamide (15 mL) at a temperature of 22–27° C. The resulting mixture was stirred at 22° C. for 1 h and poured onto ice. The aqueous phase was extracted with ethyl acetate, and the combined organic phases were washed with brine, dried (MgSO$_4$) and concentrated in vacuo. The crude product was purified by flash chromatography on silicagel (eluent:ethyl acetate/heptane/triethylamine 50:50:5) to give the product as an orange oil (2.4 g). The title compound was isolated as the oxalate salt from acetone as a white crystalline compound (0.6 g). Mp 188–189° C. ¹H NMR (DMSO-d$_6$): 1.85–2.05 (m, 4H); 2.10 (d, 2H); 2.55 (t, 2H); 2.90 (t, 2H); 2.95–3.05 (m, 3H); 3.10 (t, 2H); 3.50 (d, 2H); 3.75 (s, 3H); 3.95 (t, 2H); 6.95–7.05 (m, 2H); 7.15–7.30 (m, 4H); 7.35–7.45 (m, 2H). MS m/z: 420 (MH+), 188.

The following compounds were prepared in a similar manner 5b, 5-Fluoro-1-methyl-3-{1-[4-(2-oxo-3,4-dihydro-2H-quinolin-1-yl)butan-1-yl]piperidin-4-yl}-1H-indole, hydrochloride from 5-fluoro-3-{1-[4-(2-oxo-3,4-dihydro-2H-quinolin-1-yl)butan-1-yl]piperidin-4-yl}-1H-indole and methyl iodide. Mp 177–179° C. ¹H NMR (DMSO-d$_6$): 1.55–1.65 (m, 2H); 1.75–1.85 (m, 2H); 2.00–2.15 (m, 4H); 2.55 (t, 2H); 2.90 (t, 2H); 2.95–3.15 (m, 5H); 3.55 (d, 2H); 3.75 (s, 3H); 3.95 (t, 2H); 6.95–7.05 (m, 2H); 7.15 (d, 1H); 7.20–7.30 (m, 3H); 7.35–7.45 (m, 1H); 7.55 (d, 1H); 11.40 (broad s, 1H). MS m/z: 434 (MH+).

5c, 1-(Butan-1-yl)-5-fluoro-3-{1-[4-(2-oxo-3,4-dihydro-2H-quinolin-1-yl)butan-1-yl]-3,6-dihydro-2H-pyridin-4-yl}-1H-indole, oxalate from 5-fluoro-3-{1-[4-(2-oxo-3,4-dihydro-2H-quinolin-1-yl)butan-1-yl]-3,6-dihydro-2H-pyridin-4-yl}-1H-indole and butyl bromide. Mp 152–154° C. $^1$H NMR (DMSO-$d_6$): 0.90 (t, 3H); 1.20–1.30 (m, 2H); 1.55–1.65 (m, 2H); 1.65–1.80 (m, 4H); 2.55 (t, 2H); 2.75 (s, 2H); 2.85 (t, 2H); 3.10 (t, 2H); 3.35 (s, 2H); 3.80 (s, 2H); 3.95 (t, 2H); 4.15 (t, 2H); 6.10 (s, 1H); 6.95–7.05 (m, 2H); 7.15 (d, 1H); 7.20–7.30 (m, 2H); 7.50–7.55 (m, 1); 7.55–7.70 (m, 2H). MS m/z: 474 (MH+), 231.

Example 6

6a, 5-Fluoro-3-{1-[3-(3,4-dihydro-1H-isoquinolin-2-yl)-3-oxopropan-1-yl]piperidin-4-yl}-1H-indole, oxalate A mixture of 5-fluoro-3-(piperidin-4-yl)-1H-indole (3.0 g), butanone (200 mL), tetrahydrofuran (100 mL), methanol (50 mL) and triethylamine (2.4 mL) was heated until reflux temperature followed by the addition of a solution of 3-chloro-1-(3,4-dihydro-1H-isoquinolin-2-yl)propan-1-one (3.5 g) in butanone (60 mL). The mixture was boiled under reflux for 30 h followed by the addition of an additional amount of 3-chloro-1-(3,4-dihydro-1H-isoquinolin-2-yl)propan-1-one (2.0 g) and triethylamine (1.6 mL) in tetrahydrofuran (50 mL). The resulting mixture was boiled under reflux for an additional 12 h. The mixture was cooled, filtered and concentrated in vacuo. The residue was purified by flash chromatography on silicagel (eluent:ethyl acetate/ethanol/triethylamine 100:4:4) to give the crude product. The title compound was isolated as the oxalate salt from acetone as a white crystalline compound (0.75 g). Mp 206–209° C. $^1$H NMR (DMSO-$d_6$): 1.95 (q, 2H); 2.05–2.15 (m, 2H); 2.80 (t, 0.8H); 2.90 (t, 1.2H); 2.90–3.10 (m, 5H); 3.30 (t, 2H); 3.55 (d, 2H); 3.70 (t, 2H); 4.65 (s, 1.20H); 4.70 (s, 0.8H); 6.85–6.95 (m, 1H); 7.15–7.25 (m, 5H); 7.30–7.40 (m, 1H); 7.40 (d, 1H); 11.05 (s, 1H). MS m/z: 406 (MH+), 231.

The following compound was prepared in a similar manner 6b, 7-Chloro-3-{1-[3-(3,4-dihydro-1H-isoquinolin-2-yl)-3-oxopropan-1-yl]piperidin-4-yl}-1H-indole, hydrochloride from 7-chloro-3-(piperidin-4-yl)-1H-indole and 3-bromo-1-(3,4-dihydro-1H-isoquinolin-2-yl)propan-1-one. $^1$H NMR (DMSO-$d_6$): 2.05–2.25 (m, 4H); 2.80 (t, 0.8H); 2.95 (t, 1.2H); 3.00–3.20 (m, 5H); 3.30–3.45 (m, 2H); 3.55–3.65 (m, 2H); 3.65–3.75 (m, 2H); 4.65 (s, 1.2H); 4.75 (s, 0.8H); 7.00 (t, 1H); 7.15–7.25 (m, 6H); 7.70 (d, 1H); 10.70 (broad s, 1H); 11.30 (s, 1H). MS m/z: 422 (MH+), 247.

6c. 5-Chloro-3-{1-[4-(3,4-dihydro-2H-quinolin-1-yl)-4-oxobutan-1-yl]piperidin-4-yl}-1H-indole, hydrochloride from 5-chloro-3-(piperidin-4-yl)-1H-indole and 4-chloro-1-(3,4-dihydro-2H-quinolin-1-yl)butan-1-one. Mp 158–162° C. $^1$H NMR (DMSO-$d_6$): 1.85–1.95 (m, 2H); 1.95–2.20 (m, 6H); 2.60–2.75 (m, 4H); 2.95–3.15 (m, 5H); 3.55 (d, 2H); 3.70 (t, 2H); 7.05–7.25 (m, 6H); 7.40 (d, 1H); 7.75 (s, 1H); 10.45 (broad s, 1H); 11.15 (s, 1H). MS m/z: 436 (MH+), 303.

Example 7

7, 5-Fluoro-3-{1-[4-(3,4-dihydro-1H-isoquinolin-2-yl)-4-oxobutan-1-yl]piperidin-4-yl}-1H-indole A mixture of 5-fluoro-3-(piperidin-4-yl)-1H-indole (3.0 g), butanone (200 mL), tetrahydrofuran (200 mL), methanol (30 mL), potassium iodide (11.4 g) and triethylamine (7.6 mL) was heated until reflux temperature followed by the addition of a solution of 4-chloro-1-(3,4-dihydro-1H-isoquinolin-2-yl)butan-1-one (14.6 g) in butanone (50 mL). The mixture was boiled under reflux for 2 h, filtered hot and concentrated in vacuo. The residue was purified by flash chromatography on silicagel (eluent:ethyl acetate/ethanol/triethylamine 100:5:5) to give the crude product. The title compound was isolated as the free base from ethyl acetate as a white crystalline compound (0.9 g). Mp 146–148° C. $^1$H NMR (DMSO-$d_6$): 1.55–1.70 (m, 2H); 1.70–1.80 (m, 2H); 1.85–1.95 (m, 2H); 2.00 (q, 2H); 2.30 (q, 2H); 2.35–2.45 (m, 2H); 2.60–2.70 (m, 1H); 2.75 (t, 0.8H); 2.80–3.00 (m, 3.2H); 3.65 (t, 2H); 4.60 (s, 1.2H); 4.70 (s, 0.8H); 6.85–6.95 (m, 1H); 7.10–7.20 (m, 5H); 7.25 (d, 1H); 7.30–7.35 (m, 1H); 10.85 (s, 1H). MS m/z: 420 (MH+), 202.

Example 8

8, 5-Chloro-3-{1-[4-(3,4-dihydro-1H-isoquinolin-2-yl)-4-oxobutan-1-yl]piperidin-4-yl}-1H-indole A mixture of 5-fluoro-3-(piperidin-4-yl)-1H-indole (3.0 g), butanone (200 mL) and triethylamine (8.9 mL) was heated until reflux temperature followed by the addition of a solution of 4-chloro-1-(3,4-dihydro-1H-isoquinolin-2-yl)butan-1-one (15.2 g) in butanone (80 mL). The mixture was boiled under reflux for 6 h. The resulting mixture was filtered and concentrated in vacuo. The residue was purified by flash chromatography on silicagel (eluent:ethyl acetate/ethanol/triethylamine 100:4:4) to give the crude product. The title compound was isolated as the free base from acetone as a white crystalline compound (0.6 g). Mp 172–175° C. $^1$H NMR (DMSO-$d_6$): 1.55–1.65 (m, 2H); 1.65–1.75 (m, 2H); 1.90 (s, 2H); 2.00 (q, 2H); 2.30 (q, 2H); 2.40 (q, 2H); 2.65–2.80 (m, 1.8H); 2.80–3.00 (m, 3.2H); 3.70 (t, 2H); 4.60 (s, 1.2H); 4.70 (s, 0.8H); 7.05 (d, 1H); 7.10–7.25 (m, 5H); 7.35 (d, 1H); 7.55 (s, 1H); 11.00 (s, 1H). MS m/z: 436 (MH+), 202.

Example 9

9a, 5-Fluoro-3-{1-[3-(3,4-dihydro-2H-quinolin-1-yl)propan-1-yl]piperidin-4-yl}-1H-indole, dihydrochloride A suspension of lithium aluminium hydride (0.94 g) in tetrahydrofuran (40 mL) was stirred at 5° C. followed by the addition of concentrated sulphuric acid (1.2 g) in tetrahydrofuran (20 mL). The mixture was stirred at 7° C. for 60 min followed by the addition of 5-fluoro-3-{1-[3-(2-oxo-3,4-dihydro-2H-quinolin-1-yl)propan-1-yl]piperidin-4-yl}-1H-indole (2.0 g) in tetrahydrofuran (60 mL). The resulting mixture was stirred at 5° C. for 60 min followed by standard work up. The residue was purified by flash chromatography on silicagel (eluent:ethyl acetate) to give the crude product as a colourless oil. The title compound was isolated as the dihydrochloride salt from tetrahydrofuran as a white crystalline compound (1.0 g). Mp 230–236° C. $^1$H NMR (DMSO-$d_6$): 1.95 (t, 2H); 2.00–2.30 (m, 4H); 2.75 (t, 2H); 2.95–3.20 (m, 5H); 3.30 (t, 2H); 3.40 (t, 2H); 3.55 (d, 2H) 6.20 (broad s, 1H); 6.70 (broad s, 1H); 6.95 (m, 2H); 7.00 (d, 1H); 7.10 (t, 1H); 7.20 (s, 1H); 7.30–7.40 (m, 1H); 7.50 (d, 1H); 10.95 (broad s, 1H); 11.05 (s, 1H). MS m/z: 392 (MH+), 259.

The following compounds were prepared in a similar manner 9b, 5-Fluoro-3-{1-[4-(3,4-dihydro-2H-quinolin-1-yl)butan-1-yl]piperidin-4-yl}-1H-indole, dihydrochloride from 5-fluoro-3-{1-[4-(2-oxo-3,4-dihydro-2H-quinolin-1-yl)butan-1-yl]piperidin-4-yl}-1H-indole. Mp 207–212° C. $^1$H NMR (DMSO-$d_6$): 1.65 (s, 2H); 1.80–1.90 (m, 2H); 1.95 (s, 2H); 2.05 (d, 2H); 2.20 (q, 2H); 2.65–2.80 (m, 2H); 2.95–3.25 (m, 4H); 3.15–3.25 (m, 1H); 3.35 (s, 4H); 3.55 (d, 2H); 4.65 (broad s); 5.55–6.95 (m, 3H); 7.00 (s, 1H); 7.10 (s, 1H); 7.20 (s, 1H); 7.30–7.40 (m, 1H); 7.55 (d, 1H); 11.75 (broad s, 1H); 11.05 (s, 1H). MS m/z: 406 (MH+), 274.

9c, 5-Fluoro-3-{1-[5-(3,4-dihydro-2H-quinolin-1-yl)pentan-1-yl]piperidin-4-yl}-1H-indole, dihydrochloride from 5-fluoro-3-{1-[5-(2-oxo-3,4-dihydro-2H-quinolin-1-yl)pentan-1-yl]piperidin-4-yl}-1H-indole. Mp 155–158° C. $^1$H NMR (DMSO-d$_6$): 1.30–145 (m, 2H); 1.65 (s, 2H); 1.75–1.80 (m, 2H); 1.95 (s, 2H); 2.20 (q, 2H); 2.75 (s, 2H); 2.95–3.10 (m, 5H); 3.35 (s, 4H); 3.55 (d, 2H); 5.05 (broad s); 6.70–7.15 (m, 4H); 6.90 (t, 1H); 7.20 (s, 1H); 7.30–7.40 (m, 1H); 7.50 (d, 1H); 10.75 (broad s, 1H); 11.05 (s, 1H). MS m/z: 420 (MH+), 287.

9d, 5-Chloro-3-{1-[3-(3,4-dihydro-2H-quinolin-1-yl)propan-1-yl]piperidin-4-yl}-1H-indole, dihydrochloride from 5-chloro-3-{1-[3-(2-oxo-3,4-dihydro-2H-quinolin-1-yl)propan-1-yl]piperidin-4-yl}-1H-indole. Mp 201–204° C. $^1$H NMR (DMSO-d$_6$): 1.95 (t, 2H); 2.00–2.25 (m, 6H); 2.75 (t, 2H); 3.00–3.20 (m, 5H); 3.30 (t, 2H); 3.40 (t, 2H); 3.55 (d, 2H); 6.40 (broad s); 6.65 (s, 1H); 6.85 (s, 1H); 6.95 (d, 1H); 7.00–7.10 (m, 2H); 7.20 (s, 1H); 7.40 (d, 1H); 7.75 (s, 1H); 10.85 (broad s, 1H); 11.20 (s, 1H). MS m/z: 408 (MH+), 275.

9e, 5-Chloro-3-{1-[4-(3,4-dihydro-2H-quinolin-1-yl)butan-1-yl]piperidin-4-yl}-1H-indole, dihydrochloride from 5-chloro-3-{1-[4-(2-oxo-3,4-dihydro-2H-quinolin-1-yl)butan-1-yl]piperidin-4-yl}-1H-indole. Mp 140–145° C. $^1$H NMR (DMSO-d$_6$): 1.65 (s, 2H); 1.80–1.90 (m, 2H); 1.95 (s, 2H); 2.00–2.25 (m, 4H); 2.75 (s, 2H); 2.95–3.25 (m, 5H); 3.35 (s, 4H); 3.55 (d, 2H); 6.75 (broad s, 1H); 6.90 (broad s, 1H); 7.00 (s, 1H); 7.05–7.15 (m, 2H); 7.20 (s, 1H); 7.40 (d, 1H); 7.80 (s, 1H); 10.70 (broad s, 1H); 11.20 (s, 1H). MS m/z: 422 (MH+), 289, 188.

9f, 5-Chloro-3-{1-[5-(3,4-dihydro-2H-quinolin-1-yl)pentan-1-yl]piperidin-4-yl}-1H-indole, dihydrochloride from 5-chloro-3-{1-[5-(2-oxo-3,4-dihydro-2H-quinolin-1-yl)pentan-1-yl]piperidin-4-yl}-1H-indole. Mp 101–106° C. $^1$H NMR (DMSO-d$_6$): 1.30–1.45 (m, 2H); 1.65 (s, 2H); 1.70–1.85 (m, 2H); 1.95 (s, 2H); 2.00–2.25 (m, 4H); 2.75 (s, 2H); 2.95–3.25 (m, 5H); 3.35 (s, 4H); 3.55 (d, 2H); 6.80 (broad s, 1H); 6.90–7.15 (m, 4H); 7.20 (s, 1H); 7.35 (d, 1H); 7.75 (s, 1H); 10.70 (broad s, 1H); 11.20 (s, 1H). MS m/z: 436 (MH+), 303.

9g, 7-Chloro-3-{1-[4-(3,4-dihydro-2H-quinolin-1-yl)butan-1-yl]piperidin-4-yl}-1H-indole, dihydrochloride from 7-chloro-3-{1-[4-(2-oxo-3,4-dihydro-2H-quinolin-1-yl)butan-1-yl]piperidin-4-yl}-1H-indole. Mp 214–219° C. $^1$H NMR (DMSO-d$_6$): 1.65 (s, 2H); 1.80–1.90 (m, 2H); 1.95 (s, 2H); 2.00–2.15 (m, 2H); 2.15–2.30 (m, 2H); 2.70 (s, 2H); 2.95–3.15 (m, 5H); 3.35 (s, 4H); 3.55 (d, 2H); 6.70 (broad s, 1H); 6.85 (broad s, 1H); 6.95–7.05 (m, 2H); 7.10 (s, 1H); 7.15–7.25 (m, 2H); 7.70 (d, 1H); 10.80 (broad s, 1H); 11.30 (s, 1H). MS m/z: 422 (MH+), 289, 188.

9h, 5-Fluoro-1-methyl-3-{1-[3-(3,4-dihydro-2H-quinolin-1-yl)propan-1-yl]piperidin-4-yl}-1H-indole, dihydrochloride from 5-fluoro-1-methyl-3-{1-[3-(2-oxo-3,4-dihydro-2H-quinolin-1-yl)propan-1-yl]piperidin-4-yl}-1H-indole. Mp 202–206° C. $^1$H NMR (DMSO-d$_6$): 1.85–1.95 (m, 2H); 2.00–2.10 (m, 4H); 2.10–2.25 (m, 2H); 2.65–2.75 (m, 2H); 2.95–3.15 (m, 5H); 3.25–3.35 (m, 2H); 3.35–3.40 (m, 2H); 3.55 (d, 2H); 3.75 (s, 3H); 6.65 (broad s, 1H); 6.80 (broad s, 1H); 6.90–7.10 (m, 3H); 7.20 (s, 1H); 7.35–7.45 (m, 1H); 7.55 (d, 1H); 10.90 (broad s, 1H). MS m/z: 406 (MH+), 273.

9i, 5-Fluoro-1-methyl-3-{1-[4-(3,4-dihydro-2H-quinolin-1-yl)butan-1-yl]piperidin-4-yl}-1H-indole, oxalate from 5-fluoro-1-methyl-3-{1-[4-(2-oxo-3,4-dihydro-2H-quinolin-1-yl)butan-1-yl]piperidin-4-yl}-1H-indole. Mp 123–125° C. $^1$H NMR (DMSO-d$_6$): 1.50–1.60 (m, 2H); 1.65–1.75 (m, 2H); 1.80–1.90 (m, 2H); 1.90–2.00 (m, 2H); 2.10 (d, 2H); 2.60–2.70 (m, 2H); 2.95–3.10 (m, 5H); 3.20–3.30 (m, 4H); 3.50 (d, 2H); 3.75 (s, 3H); 6.45 (t, 1H); 6.60 (d, 1H); 6.85 (d, 1H); 6.95–7.05 (m, 2H); 7.20 (s, 1H); 7.40–7.45 (m, 2H). MS m/z: 420 (MH+), 287.

9j, 5-Fluoro-3-{1-[4-(3,4-dihydro-2H-1,4-benzoxazin-4-yl)butan-1-yl]piperidin-4-yl}-1H-indole, dihydrochloride from 5-fluoro-3-{1-[4-(3-oxo-3,4-dihydro-2H-1,4-benzoxazin-4-yl)butan-1-yl]piperidin-4-yl}-1H-indole. Mp 179–186° C. $^1$H NMR (DMSO-d$_6$): 1.55–1.65 (m, 2H); 1.75–1.90 (m, 2H); 2.00–2.10 (m, 2H); 2.15–2.25 (m, 2H); 2.95–3.25 (m, 5H); 3.25–3.40 (m, 4H); 3.55 (d, 2H); 4.15–4.25 (m, 2H); 6.55 (t, 1H); 6.65 (d, 1H); 6.70–6.80 (m, 2H); 6.90 (t, 1H); 7.20 (s, 1H); 7.30–7.40 (m, 1H); 7.55 (d, 1H); 10.80 (broad s, 1H); 11.05 (s, 1H). MS m/z: 408 (MH+), 273, 190.

9k, 5-Chloro-3-{1-[4-(3,4-dihydro-2H-1,4-benzoxazin-4-yl)butan-1-yl]piperidin-4-yl}-1H-indole, dihydrochloride from 5-chloro-3-{1-[4-(3-oxo-3,4-dihydro-2H-1,4-benzoxazin-4-yl)butan-1-yl]piperidin-4-yl}-1H-indole. Mp 186–190° C. $^1$H NMR (DMSO-d$_6$): 1.55–1.65 (m, 2H); 1.70–1.85 (m, 2H); 2.00–2.20 (m, 4H); 2.95–3.25 (m, 5H); 3.25–3.40 (m, 4H); 3.55 (d, 2H); 4.15–4.20 (m, 2H); 6.55 (t, 1H); 6.65 (d, 1H); 6.70–6.80 (m, 2H); 7.05 (d, 1H); 7.20 (s, 1H); 7.40 (d, 1H); 7.75 (s, 1H); 10.50 (broad s, 1H); 11.15 (s, 1H). MS m/z: 424 (MH+), 289, 190.

9l, 5-Fluoro-3-{1-[3-(3,4-dihydro-2H-quinolin-1-yl)propan-1-yl]-3,6-dihydro-2H-pyridin-4-yl}-1H-indole, dihydrochloride from 5-fluoro-3-{1-[3-(2-oxo-3,4-dihydro-2H-quinolin-1-yl)propan-1-yl]-3,6-dihydro-2H-pyridin-4-yl}-1H-indole. Mp 220–223° C. $^1$H NMR (DMSO-d$_6$): 1.85–2.00 (m, 2H); 2.05–2.10 (m, 2H); 2.70–2.80 (m, 4H); 2.90–3.00 (m, 1H); 3.15–3.30 (m, 2H); 3.30–3.35 (m, 2H); 3.40 (t, 2H); 3.55–3.65 (m, 1H); 3.70–3.80 (m, 1H); 4.00 (d, 1H); 6.10 (s, 1H); 6.70 (broad s, 1H); 6.90 (broad s, 1H); 6.95–7.05 (m, 2H); 7.05–7.10 (m, 1H); 7.40–7.45 (m, 1H); 7.55–7.65 (m, 2H); 11.10 (broad s, 1H); 11.60 (s, 1H). MS m/z: 390 (MH+), 203, 146.

9m, 5-Fluoro-3-{1-[4-(3,4-dihydro-2H-quinolin-1-yl)butan-1-yl]-3,6-dihydro-2H-pyridin-4-yl}-1H-indole, dihydrochloride from 5-fluoro-3-{1-[4-(2-oxo-3,4-dihydro-2H-quinolin-1-yl)butan-1-yl]-3,6-dihydro-2H-pyridin-4-yl}-1H-indole. Mp 198–200° C. $^1$H NMR (DMSO-d$_6$): 1.60–1.75 (m, 2H); 1.80–1.90 (m, 2H); 1.95 (s, 2H); 2.70–2.80 (m, 4H); 2.85–3.00 (m, 1H); 3.15–3.30 (m, 4H); 3.30–3.40 (m, 2H); 3.55–3.65 (m, 1H); 3.70–3.80 (m, 1H); 3.95 (d, 1H); 6.10 (s, 1H); 6.80 (broad s, 1H); 6.90–7.20 (m, 3H); 7.00 (t, 1H); 7.40–7.45 (m, 1H); 7.55–7.65 (m, 2H); 10.95 (broad s, 1H); 11.55 (s, 1H). MS m/z: 404 (MH+), 271, 217.

9n, 5-Fluoro-3-{1-[5-(3,4-dihydro-2H-quinolin-1-yl)pentan-1-yl]-3,6-dihydro-2H-pyridin-4-yl}-1H-indole, dihydrochloride from 5-fluoro-3-{1-[5-(2-oxo-3,4-dihydro-2H-quinolin-1-yl)pentan-1-yl]-3,6-dihydro-2H-pyridin-4-yl}-1H-indole. Mp 167–169° C. $^1$H NMR (DMSO-d$_6$): 1.30–1.45 (m, 2H); 1.70 (s, 2H); 1.75–1.90 (m, 2H); 2.00 (s, 2H); 2.70–2.85 (m, 3H); 2.85–3.00 (m, 1H); 3.05–3.20 (m, 2H); 3.20–3.30 (m, 1H); 3.35 (s, 2H); 3.55–3.65 (m, 1H); 3.70–3.80 (m, 1H); 3.95 (d, 1H); 6.10 (s, 1H); 6.80–7.25 (m, 4H); 7.00 (t, 1H); 7.40–7.45 (m, 1H); 7.55–7.65 (m, 2H); 11.00 (s, broad s, 1H); 11.60 (s, 1H). MS m/z: 418 (MH+), 231, 188.

Example 10

10a, 4-Fluoro-3-{1-[3-(3,4-dihydro-1H-isoquinolin-2-yl)-3-oxopropan-1-yl]piperidin-4-yl}-1H-indole Polymer bound 3-[1-(4-fluoro-1H-indol-3-yl)piperidin-1-yl)propionic acid (0.1 g, 0.08 mmol) and dry dichloromethane (1 mL) were mixed in a reactor tube. The mixture was cooled to 0° C. and treated for 2 h with a 2 M solution of thionyl chloride (0.4 mL, 0.8 mmol) in dichloromethane. The resin was filtered off and washed with dry dichloromethane (3×1 mL), resuspended in dichloromethane (1 mL), and treated for 3 h at room temperature with 3,4-dihydro-1H-isoquinoline (0.05 g, 0.4 mmol). The resin was filtered off and washed with dichloromethane (3×1 mL), a 1:1 mixture of dichloromethane:triethylamine (3×1 mL) and dry dichloromethane (3×1 mL). The resin was treated for 1 h with 1 mL of a mixture of sodium methoxide (2 mL, 5 N sodium methoxide in methanol), methanol (50 mL) and tetrahydrofuran (50 mL). After filtration, the resin was washed with methanol (1 mL). The combined filtrates were loaded on a pre-conditioned ion exchange column (500 mg SCX column, commercially available from Analytical Instruments, part no. 1210-2040), washed with acetonitrile (1 mL) and methanol (1 mL). The product was eluted with 4 M ammonia in methanol. After evaporation of volatile solvents, the crude product was purified by preparative reversed phase HPLC chromatography. The resulting solution was subsequently loaded on a pre-conditioned ion exchange column washed with acetonitrile (1 mL) and methanol (1 mL). The product was eluted with 4 M ammonia in methanol. Evaporation of volatile solvents afforded the title compound as an yellow oil (5 mg, 12 μmol). LC/MS (m/z) 406 (MH+), RT=3.61, purity: 66%.

The following compounds were prepared in a similar manner (10b–10m) or by the use of 3,4-dihydro-2H-quinoline (10n–10z):

10b, 4-Fluoro-3-{1-[4-(3,4-dihydro-1H-isoquinolin-2-yl)-4-oxobutan-1-yl]piperidin-4-yl}-1H-indole
  LC/MS (m/z) 420 (MH+), RT=3.69, purity: 93%
10c, 4-Fluoro-3-{1-[6-(3,4-dihydro-1H-isoquinolin-2-yl)-6-oxohexan-1-yl]piperidin-4-yl}-1H-indole
  LC/MS (m/z) 448 (MH+), RT=3.81, purity: 97%
10d, 4-Chloro-3-{1-[4-(3,4-dihydro-1H-isoquinolin-2-yl)-4-oxobutan-1-yl]piperidin-4-yl}-1H-indole
  LC/MS (m/z) 436 (MH+), RT=3.86, purity: 97%
10e, 4-Chloro-3-{1-[5-(3,4-dihydro-1H-isoquinolin-2-yl)-5-oxopentan-1-yl]piperidin-4-yl}-1H-indole
  LC/MS (m/z) 450 (MH+), RT=3.87, purity: 81%
10f, 4-Chloro-3-{1-[6-(3,4-dihydro-1H-isoquinolin-2-yl)-6-oxohexan-1-yl]piperidin-4-yl}-1H-indole
  LC/MS (m/z) 464 (MH+), RT=3.97, purity: 86%
10g, 5-Fluoro-3-{1-[5-(3,4-dihydro-1H-isoquinolin-2-yl)-5-oxopentan-1-yl]piperidin-4-yl}-1H-indole
  LC/MS (m/z) 434 (MH+), RT=3.67, purity: 93%
10h, 5-Fluoro-3-{1-[6-(3,4-dihydro-1H-isoquinolin-2-yl)-6-oxohexan-1-yl]piperidin-4-yl}-1H-indole
  LC/MS (m/z) 448 (MH+), RT=3.79, purity: 89%
10i, 6-Chloro-3-{1-[3-(3,4-dihydro-1H-isoquinolin-2-yl)-3-oxopropan-1-yl]piperidin-4-yl}-1H-indole
  LC/MS (m/z) 422 (MH+), RT=3.80, purity: 85%
10j, 6-Chloro-3-{1-[6-(3,4-dihydro-1H-isoquinolin-2-yl)-6-oxohexan-1-yl]piperidin-4-yl}-1H-indole
  LC/MS (m/z) 464 (MH+), RT=3.98, purity: 87%
10k, 7-Chloro-3-{1-[4-(3,4-dihydro-1H-isoquinolin-2-yl)-4-oxobutan-1-yl]piperidin-4-yl}-1H-indole
  LC/MS (m/z) 436 (MH+), RT=3.85, purity: 98%
10l, 7-Chloro-3-{1-[5-(3,4-dihydro-1H-isoquinolin-2-yl)-5-oxopentan-1-yl]piperidin-4-yl}-1H-indole
  LC/MS (m/z) 450 (MH+), RT=3.85, purity: 96%
10m, 7-Chloro-3-{1-[6-(3,4-dihydro-1H-isoquinolin-2-yl)-6-oxohexan-1-yl]piperidin-4-yl}-1H-indole
  LC/MS (m/z) 464 (MH+), RT=3.96, purity: 97%
10n, 4-Fluoro-3-{1-[3-(3,4-dihydro-2H-quinolin-1-yl)-3-oxopropan-1-yl]piperidin-4-yl}-1H-indole
  LC/MS (m/z) 406 (MH+), RT=3.67, purity: 82%
10o, 4-Fluoro-3-{1-[4-(3,4-dihydro-2H-quinolin-1-yl)-4-oxobutan-1-yl]piperidin-4-yl}-1H-indole
  LC/MS (m/z) 420 (MH+), RT=3.78, purity: 84%
10p, 4-Chloro-3-{1-[3-(3,4-dihydro-2H-quinolin-1-yl)-3-oxopropan-1-yl]piperidin-4-yl}-1H-indole
  LC/MS (m/z) 422 (MH+), RT=3.85, purity: 97%
10q, 4-Chloro-3-{1-[4-(3,4-dihydro-2H-quinolin-1-yl)-4-oxobutan-1-yl]piperidin-4-yl}-1H-indole
  LC/MS (m/z) 436 (MH+), RT=3.97, purity: 92%
10r, 5-Fluoro-3-{1-[3-(3,4-dihydro-2H-quinolin-1-yl)-3-oxopropan-1-yl]piperidin-4-yl}-1H-indole
  LC/MS (m/z) 406 (MH+), RT=3.63, purity: 97%
10s, 5-Fluoro-3-{1-[4-(3,4-dihydro-2H-quinolin-1-yl)-4-oxobutan-1-yl]piperidin-4-yl}-1H-indole
  LC/MS (m/z) 420 (MH+), RT=3.73, purity: 96%
10t, 5-Fluoro-3-{1-[5-(3,4-dihydro-2H-quinolin-1-yl)-5-oxopentan-1-yl]piperidin-4-yl}-1H-indole
  LC/MS (m/z) 434 (MH+), RT=3.76, purity: 97%
10u, 5-Fluoro-3-{1-[6-(3,4-dihydro-2H-quinolin-1-yl)-6-oxohexan-1-yl]piperidin-4-yl}-1H-indole
  LC/MS (m/z) 448 (MH+), RT=3.88, purity: 97%
10v, 6-Chloro-3-{1-[3-(3,4-dihydro-2H-quinolin-1-yl)-3-oxopropan-1-yl]piperidin-4-yl}-1H-indole
  LC/MS (m/z) 422 (MH+), RT=3.88, purity: 90%
10w, 6-Chloro-3-{1-[6-(3,4-dihydro-2H-quinolin-1-yl)-6-oxohexan-1-yl]piperidin-4-yl}-1H-indole
  LC/MS (m/z) 464 (MH+), RT=4.09, purity: 96%
10x, 7-Chloro-3-{1-[4-(3,4-dihydro-2H-quinolin-1-yl)-4-oxobutan-1-yl]piperidin-4-yl}-1H-indole
  LC/MS (m/z) 436 (MH+), RT=3.91, purity: 98%
10y, 7-Chloro-3-{1-[5-(3,4-dihydro-2H-quinolin-1-yl)-5-oxopentan-1-yl]piperidin-4-yl}-1H-indole
  LC/MS (m/z) 450 (MH+), RT=3.93, purity: 96%
10z, 7-Chloro-3-{1-[6-(3,4-dihydro-2H-quinolin-1-yl)-6-oxohexan-1-yl]piperidin-4-yl}-1H-indole
  LC/MS (m/z) 464 (MH+), RT=4.05, purity: 97%

Example 11

11a, 5-Fluoro-3-{1-[4-(3,4-dihydro-1H-isoquinolin-2-yl) butan-1-yl]piperidin-4-yl}-1H-indole, dioxalate A mixture of 5-fluoro-3-(piperidin-4-yl)-1H-indole (5.0 g), triethylamine (6.35 mL) and tetrahydrofuran (500 mL) was cooled to 7° C. and subsequently added a mixture of succinic anhydride (2.5 g) in tetrahydrofuran (50 mL). The mixture was stirred at 8–10° C. for 2 h, and the solvent was removed in vacuo. The residue was dissolved in ethyl acetate, and the organic phase was washed with cold 2N aqueous hydrochloride solution and brine. The organic phase was dried (MgSO$_4$), filtered and concentrated in vacuo (6.4 g). The residue (1.5 g) and 3,4-dihydro-1H-isoquinoline (0.63 g) was dissolved in a mixture of acetonitril (25 mL) and dimethyl formamide (10 mL), and the resulting mixture was cooled (5° C.) and subsequently added 1,3-dicyclohexylcarbodiimide (1.0 g). The mixture was stirred at room temperature for 16 h, filtered and poured into brine. The aqueous phase was extracted with ethyl acetate and tetrahydrofuran, and the combined organic phase was washed with brine, dried (MgSO$_4$) and concentrated in vacuo. The residue was purified by flash chromatography on silicagel (eluent:ethyl acetate) to give a white solid (1.0 g), which subsequently was added to a mixture of alane in tetrahydrofuran (100 mL) at 5–10° C. The alane was prepared from lithium aluminium hydride (0.55 g) and concentrated sulphuric acid (0.72 g). The mixture was quenched by the addition of water (1 mL), 15% aqueous sodium hydroxide solution (0.5 mL) and water (2.5 mL), and the resulting mixture was dried (MgSO$_4$), filtered and concentrated in vacuo. The title compounds was crystallised from acetone as the dioxalate salt (0.8 g). Mp 105–111° C. $^1$H NMR (DMSO-d$_6$): 1.75 (s, 4H); 1.85–2.05 (m, 2H); 2.10 (d, 2H); 2.90–3.20 (m, 9H); 3.25 (t, 2H); 3.50 (d, 2H); 4.15 (s, 2H); 6.85–6.95 (m, 1H); 7.10–7.25 (m, 5H); 7.30–7.45 (m, 2H); 11.05 (s, 1H). MS m/z: 406 (MH+), 273, 188.

The following compound was prepared in a similar manner 11b, 5-Fluoro-3-{1-[4-(6,7-dimethoxy-3,4-dihydro-1H-isoquinolin-2-yl)butan-1-yl]piperidin-4-yl}-1H-indole, dioxalate from 5-fluoro-3-(piperidin-4-yl)-1H-indole and 6,7-dimethoxy-3,4-dihydro-1H-isoquinoline. Mp 98–105° C. $^1$H NMR (DMSO-d$_6$): 1.75 (s, 4H); 1.85–2.00 (m, 2H); 2.10 (d, 2H); 2.90–3.15 (m, 9H); 3.30 (s, 2H); 3.50 (d, 2H); 3.75 (d, 6H); 4.10 (s, 2H); 6.75 (s, 1H); 6.80 (s, 1H); 6.90–6.95 (m, 1H); 7.20 (s, 1H); 7.30–7.45 (m, 2H); 11.05 (s, 1H). MS m/z: 466 (MH+), 273, 248.

Pharmacological Testing

The compounds of the invention were tested in well-recognised and reliable tests. The tests were as follows:

Inhibition of the Binding of [$^3$H]YM-09151-2 to Human Dopamine D$_4$ Receptors By this method, the inhibition by drugs of the binding of [$^3$H]YM-09151-2 (0.06 nM) to membranes of human cloned dopamine D$_{4.2}$ receptors expressed in CHO-cells is determined in vitro. Method modified from NEN Life Science Products, Inc., technical data certificate PC2533-10/96.

In table 1 below, the test results are shown:

TABLE 1

Binding Data (IC$_{50}$ values in nM or % inhibition of binding at 50 nM) (nt. means not tested)

| Comp. No. | D$_4$-bind. |
|---|---|
| 1a | 92% |
| 1b | 97% |
| 1c | 95% |
| 2a | 0.58 |
| 2b | 12 |
| 2c | 0.69 |
| 2d | 8.0 |
| 2e | 12 |
| 2f | 78% |
| 2g | 7.5 |
| 2h | 10 |
| 3a | 0.71 |
| 3b | 5.0 |
| 3c | 15 |
| 4 | 4.8 |
| 9l | 0.51 |
| 9m | 17 |
| 9n | 53 |
| 10a | 93% |
| 10b | 81% |
| 10c | 21% |
| 10d | 86% |
| 10e | 25% |
| 10f | 17% |
| 10g | 65% |
| 10h | 50% |
| 10i | 94% |
| 10j | 70% |
| 10k | 95% |
| 10l | 82% |
| 10m | 69% |

The compounds of the invention have been found potently to inhibit the binding of tritiated YM-09151-2 to dopamine D$_4$ receptors.

The compounds have also been tested in a functional assay described by Gazi et al. in *British Journal of Pharmacology* 1999, 128, 613–620. In this test, the compounds were shown to be partial agonists or antagonists at the dopamine D$_4$ receptors.

The compounds of the invention have also been tested in the following tests:

Inhibition of the Binding of [$^3$H]Spiperone to D$_2$ Receptors

The compounds of the invention were tested with respect to affinity for the dopamine D$_2$ receptor by determining their ability to inhibit the binding of [$^3$H]spiperone to D$_2$ receptors by the method of Hyttel et al. *J. Neurochem.* 1985, 44, 1615.

Inhibition of the Binding of [$^3$H]Spiperone to Human D$_3$ Receptors

By this method, the inhibition by drugs of the binding [$^3$H]Spiperone (0.3 nM) to membranes of human cloned dopamine D$_3$ receptors expressed in CHO-cells is determined in vitro. Method modified from MacKenzie et al. *Eur. J Pharm.-Mol. Pharm. Sec.* 1994, 266, 79–85.

Inhibition of the Uptake of [$^3$H]Serotonin into Whole Rat Brain Synaptosomes

The compounds were tested with respect to their 5-HT reuptake inhibiting effect by measuring their ability to inhibit the uptake of [$^3$H]serotonin into whole rat brain synaptosomes in vitro. The assay was performed as described by Hyttel *Psychopharmacology* 1978, 60, 13.

Inhibition of the Binding of [$^3$H]Ketanserin to 5-HT$_{2A}$ Receptors

The compounds were tested with respect to their affinity for 5-HT$_{2A}$ receptors by determining their ability to inhibit the binding of [$^3$H]Ketanserin (0.50 nM) to membranes from rat brain (cortex) in vitro. Method described in Sánchez et al. *Drug Dev. Res.* 1991, 22, 239–250.

5-HT$_{2C}$ Receptor Efficacy as Determined by Fluorometry

The compounds were tested with respect to their efficacy on 5-HT$_{2C}$ receptor-expressing CHO cells as determined by fluorometric imaging plate reader (FLIPR) analysis. This assay was carried out according to Molecular Devices Inc. instructions for their FLIPR Calcium Assay Kit and as modified from Porter et al. *British Journal of Pharmacology* 1999, 128:13.

The compounds were found to have no substantial or only weak affinity for the dopamine D$_2$ receptor.

Many of the compounds have been found to inhibit the binding of [$^3$H]Spiperone to the dopamine D$_3$ receptor, some of the compounds have been found to inhibit serotonin reuptake and some of the compounds have been found to be 5-HT$_{2A}$ receptor ligands and/or 5-HT$_{2C}$ receptor ligands.

As mentioned above, the compounds of the invention have a good aqueous solubility as compared to related compounds disclosed in WO 98/28293. Accordingly, the compounds are expected to have improved bioavailability.

Thus, the compounds of the invention are considered useful in the treatment of positive and negative symptoms of schizophrenia, other psychoses, anxiety disorders, such as generalised anxiety disorder, panic disorder, and obsessive compulsive disorder, depression, side effects induced by conventional antipsychotic agents, migraine, ADHD and in the improvement of sleep. In particular, the compounds of the invention are considered useful in the treatment of positive and negative symptoms of schizophrenia without inducing extrapyramidal side effects.

Formulation Examples

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

Typical examples of recipes for the formulation of the invention are as follows:

| 1) Tablets containing 5.0 mg of a compound of the invention calculated as the free base: | |
|---|---|
| Compound | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |
| 2) Tablets containing 0.5 mg of a compound of the invention calculated as the free base: | |
| Compound | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |
| 3) Syrup containing per milliliter: | |
| Compound | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 ml |
| Flavour | 0.05 mg |
| Saccharin sodium | 0.5 mg |
| Water | ad 1 ml |
| 4) Solution for injection containing per milliliter: | |
| Compound | 0.5 mg |
| Sorbitol | 5.1 mg |
| Acetic Acid | 0.05 mg |
| Saccharin sodium | 0.5 mg |
| Water | ad 1 ml |

What is claimed is:

1. A compound of formula I

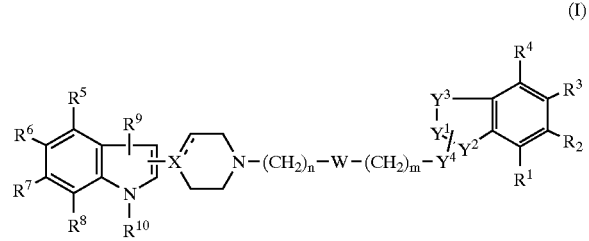

(I)

wherein
(a) one of $Y^1$ and $Y^2$ is N, which is bound to $Y^4$, and the other of $Y^1$ and $Y^2$ is CO, CS, SO, or $SO_2$ and $Y^4$ is $CH_2$;
(b) one of $Y^1$ and $Y^2$ is N, which is bound to $Y^4$, and the other of $Y^1$ and $Y^2$ is $CH_2$ and $Y^4$ is CO, CS, SO or $SO_2$; or
(c) one of $Y^1$ and $Y^2$ is N, which is bound to $Y^4$, and the other of $Y^1$ and $Y^2$ is $CH_2$ and $Y^4$ is $CH_2$;
$Y^3$ is $Z-CH_2$, $CH_2-Z$ or $CH_2CH_2$, and Z is O or S; provided that when $Y^1$ is N, $Y^3$ may not be $Z-CH_2$;
W is a bond or an O, S, CO, CS, SO or $SO_2$ group;
n is 0–5, m is 0–5 and m+n is 1 to 10; provided that when W is O or S, then n≥2 and m≥1; when W is CO, CS, SO or $SO_2$, then n≥1 and m≥1;
X is C or CH provided that when X is C, the dotted line indicates a bond, and when X is CH, the dotted line is absent;
$R^1$—$R^9$ are independently selected from hydrogen, halogen, cyano, nitro, amino, hydroxy, $C_{1-6}$-alkyl-amino, di-$C_{1-6}$-alkyl-amino, $C_{1-6}$-alkyl, $C_{2-6}$-alkenyl, $C_{2-6}$-alkynyl, $C_{1-6}$ alkoxy, $C_{1-6}$-alkylthio, $C_{1-6}$-alkyl substituted with hydroxy or thiol, $C_{3-8}$-cycloalkyl, $C_{3-8}$-cycloalkyl-$C_{1-6}$-alkyl, acyl, thioacyl, aryl, trifluoromethyl, trifluoromethylsulfonyl, and $C_{1-6}$ alkylsulfonyl;
$R^{10}$ is hydrogen, $C_{1-6}$-alkyl, $C_{2-6}$-alkenyl, $C_{2-6}$-alkynyl, $C_{1-6}$-alkyl substituted with hydroxy or thiol, $C_{3-8}$-cycloalkyl, $C_{3-8}$-cycloalkyl-$C_{1-6}$-alkyl, aryl, aryl-$C_{1-6}$-alkyl, acyl, thioacyl, $C_{1-6}$-alkylsulfonyl, trifluoromethylsulfonyl or arylsulfonyl, or a pharmaceutically acceptable acid addition salt thereof.

2. A compound according to claim 1 wherein the indole is bound to X via position 3 of the indole.

3. A compound according to claim 1 or 2 wherein one of $Y^1$ and $Y^2$ is N, which is bound to $Y^4$, and the other of $Y^1$ and $Y^2$ is CO, and $Y^4$ is $CH_2$.

4. A compound according to claim 1 or 2 wherein one of $Y^1$ and $Y^2$ is N, which is bound to $Y^4$, and the other of $Y^1$ and $Y^2$ is $CH_2$ and $Y^4$ is CO.

5. A compound according to claim 1 or 2 wherein $Y^1$ is a nitrogen bound to $Y^4$ and one of $Y^4$ and $Y^2$ is CO and the other is $CH_2$.

6. A compound according to claim 3 wherein $Y^1$ is a nitrogen bound to $Y^4$, $Y^2$ is CO and $Y^4$ is $CH_2$.

7. A compound according to claim 5 wherein $Y^1$ is a nitrogen bound to $Y^4$, $Y^2$ is CO and $Y^4$ is $CH_2$.

8. A compound according to claim 4 wherein $Y^1$ is a nitrogen bound to $Y^4$, $Y^2$ is $CH_2$ and $Y^4$ is CO.

9. A compound according to claim 5 wherein $Y^1$ is a nitrogen bound to $Y^4$, $Y^2$ is $CH_2$ and $Y^4$ is CO.

10. A compound according to claim 1 or 2 wherein $Y^2$ is a nitrogen bound to $Y^4$ and one of $Y^1$ and $Y^4$ is CO and the other is $CH_2$.

11. A compound according to claim 4 wherein $Y^2$ is a nitrogen bound to $Y^4$, $Y^1$ is $CH_2$ and $Y^4$ is CO.

12. A compound according to claim 10 wherein $Y^2$ is a nitrogen bound to $Y^4$, $Y^1$ is $CH_2$ and $Y^4$ is CO.

13. A compound according to claim 3 wherein $Y^2$ is a nitrogen bound to $Y^4$, $Y^1$ is CO and $Y^4$ is $CH_2$.

14. A compound according to claim 10 wherein $Y^2$ is a nitrogen bound to $Y^4$, $Y^1$ is CO and $Y^4$ is $CH_2$.

15. A compound according to claim 1 or 2 wherein one of $Y^1$ and $Y^2$ is N, which is bound to $Y^4$, and the other of $Y^1$ and $Y^2$ is $CH_2$ and $Y^4$ is $CH_2$.

16. A compound according to claim 1 wherein $Y^3$ is $CH_2CH_2$ or $CH_2Z$.

17. A compound according to claim 1 wherein X is C.

18. A compound according to claim 1 wherein X is CH.

19. A compound according to claim 1 wherein $R^1$—$R^9$ are independently selected from hydrogen, halogen, cyano, nitro, amino, $C_{1-6}$-alkylamino, di-$C_{1-6}$-alkylamino, $C_{1-6}$-alkyl, $C_{3-8}$-cycloalkyl and trifluoromethyl, and $R^{10}$ is hydrogen, $C_{1-6}$-alkyl or acyl, or a pharmaceutically acceptable acid addition salt thereof.

20. A compound according to claim 1 wherein W is a bond and n+m is 1 to 6.

21. A compound according to claim 20 wherein n+m is 3 to 6.

22. A compound according to claim 1 which is selected from:

5-Fluoro-3-{1-[2-(2-oxo-3,4-dihydro-2H-quinolin-1-yl)ethyl]piperidin-4-yl}-1H-indole;

5-Fluoro-3-{1-[3-(1-oxo-3,4-dihydro-1H-quinolin-2-yl)propan-1-yl]piperidin-4-yl}-1H-indole;

5-Fluoro-3-{1-[4-(1-oxo-3,4-dihydro-1H-quinolin-2-yl)butan-1-yl]piperidin-4-yl}-1H-indole;

5-Fluoro-3-{1-[3-(2-oxo-3,4-dihydro-2H-quinolin-1-yl)propan-1-yl]piperidin-4-yl}-1H-indole;

5-Fluoro-3-{1-[5-(2-oxo-3,4-dihydro-2H-quinolin-1-yl)pentan-1-yl]piperidin-4-yl}-1H-indole;

5-Chloro-3-{1-[3-(2-oxo-3,4-dihydro-2H-quinolin-1-yl)propan-1-yl]piperidin-4-yl}-1H-indole;

5-Chloro-3-{1-[4-(2-oxo-3,4-dihydro-2H-quinolin-1-yl)butan-1-yl]piperidin-4-yl}-1H-indole;

5-Chloro-3-{1-[5-(2-oxo-3,4-dihydro-2H-quinolin-1-yl)pentan-1-yl]piperidin-4-yl}-1H-indole;

7-Chloro-3-{1-[4-(2-oxo-3,4-dihydro-2H-quinolin-1-yl)butan-1-yl]piperidin-4-yl}-1H-indole;

5-Fluoro-3-{1-[4-(3-oxo-3,4-dihydro-2H-1,4-benzoxazin-4-yl)butan-1-yl]piperidin-4-yl}-1H-indole;

5-Chloro-3-{1-[4-(3-oxo-3,4-dihydro-2H-1,4-benzoxazin-4-yl)butan-1-yl]piperidin-4-yl}-1H-indole;

5-Fluoro-3-{1-[3-(2-oxo-3,4-dihydro-2H-quinolin-1-yl)propan-1-yl]-3,6-dihydro-2H-pyridin-4-yl}-1H-indole;

5-Fluoro-3-{1-[4-(2-oxo-3,4-dihydro-2H-quinolin-1-yl)butan-1-yl]-3,6-dihydro-2H-pyridin-4-yl}-1H-indole;

5-Fluoro-3-{1-[5-(2-oxo-3,4-dihydro-2H-quinolin-1-yl)pentan-1-yl]-3,6-dihydro-2H-pyridin-4-yl}-1H-indole;

5-Fluoro-3-{1-[4-(2-oxo-3,4-dihydro-2H-quinolin-1-yl)butan-1-yl]piperidin-4-yl}-1H-indole;

5-Fluoro-1-methyl-3-{1-[3-(2-oxo-3,4-dihydro-2H-quinolin-1-yl)propan-1-yl]piperidin-4-yl}-1H-indole;

5-Fluoro-1-methyl-3-{1-[4-(2-oxo-3,4-dihydro-2H-quinolin-1-yl)butan-1-yl]piperidin-4-yl}-1H-indole;

1-(Butan-1-yl)-5-fluoro-3-{1-[4-(2-oxo-3,4-dihydro-2H-quinolin-1-yl)butan-1-yl]-3,6-dihydro-2H-pyridin-4-yl}-1H-indole;

5-Fluoro-3-{1-[3-(3,4-dihydro-1H-isoquinolin-2-yl)-3-oxopropan-1-yl]piperidin-4-yl}-1H-indole;

7-Chloro-3-{1-[3-(3,4-dihydro-1H-isoquinolin-2-yl)-3-oxopropan-1-yl]piperidin-4-yl}-1H-indole;

5-Chloro-3-{1-[4-(3,4-dihydro-2H-quinolin-1-yl)-4-oxobutan-1-yl]piperidin-4-yl}-1H-indole;

5-Fluoro-3-{1-[4-(3,4-dihydro-1H-isoquinolin-2-yl)-4-oxobutan-1-yl]piperidin-4-yl}-1H-indole;

5-Chloro-3-{1-[4-(3,4-dihydro-1H-isoquinolin-2-yl)-4-oxobutan-1-yl]piperidin-4-yl}-1H-indole;

5-Fluoro-3-{1-[3-(3,4-dihydro-2H-quinolin-1-yl)propan-1-yl]piperidin-4-yl}-1H-indole;

5-Fluoro-3-{1-[4-(3,4-dihydro-2H-quinolin-1-yl)butan-1-yl]piperidin-4-yl}-1H-indole;

5-Fluoro-3-{1-[5-(3,4-dihydro-2H-quinolin-1-yl)pentan-1-yl]piperidin-4-yl}-1H-indole;

5-Chloro-3-{1-[3-(3,4-dihydro-2H-quinolin-1-yl)propan-1-yl]piperidin-4-yl}-1H-indole;

5-Chloro-3-{1-[4-(3,4-dihydro-2H-quinolin-1-yl)butan-1-yl]piperidin-4-yl}-1H-indole;

5-Chloro-3-{1-[5-(3,4-dihydro-2H-quinolin-1-yl)pentan-1-yl]piperidin-4-yl}-1H-indole;

7-Chloro-3-{1-[4-(3,4-dihydro-2H-quinolin-1-yl)butan-1-yl]piperidin-4-yl}-1H-indole;

5-Fluoro-1-methyl-3-{1-[3-(3,4-dihydro-2H-quinolin-1-yl)propan-1-yl]piperidin-4-yl}-1H-indole;

5-Fluoro-1-methyl-3-{1-[4-(3,4-dihydro-2H-quinolin-1-yl)butan-1-yl]piperidin-4-yl}-1H-indole;

5-Fluoro-3-{1-[4-(3,4-dihydro-2H-1,4-benzoxazin-4-yl)butan-1-yl]piperidin-4-yl}-1H-indole;

5-Chloro-3-{1-[4-(3,4-dihydro-2H-1,4-benzoxazin-4-yl)butan-1-yl]piperidin-4-yl}-1H-indole;

5-Fluoro-3-{1-[3-(3,4-dihydro-2H-quinolin-1-yl)propan-1-yl]-3,6-dihydro-2H-pyridin-4-yl}-1H-indole;

5-Fluoro-3-{1-[4-(3,4-dihydro-2H-quinolin-1-yl)butan-1-yl]-3,6-dihydro-2H-pyridin-4-yl}-1H-indole;

5-Fluoro-3-{1-[5-(3,4-dihydro-2H-quinolin-1-yl)pentan-1-yl]-3,6-dihydro-2H-pyridin-4-yl}-1H-indole;

4-Fluoro-3-{1-[3-(3,4-dihydro-1H-isoquinolin-2-yl)-3-oxopropan-1-yl]piperidin-4-yl}-1H-indole;

4-Fluoro-3-{1-[4-(3,4-dihydro-1H-isoquinolin-2-yl)-4-oxobutan-1-yl]piperidin-4-yl}-1H-indole;

4-Fluoro-3-{1-[6-(3,4-dihydro-1H-isoquinolin-2-yl)-6-oxohexan-1-yl]piperidin-4-yl}-1H-indole;

4-Chloro-3-{1-[4-(3,4-dihydro-1H-isoquinolin-2-yl)-4-oxobutan-1-yl]piperidin-4-yl}-1H-indole;

4-Chloro-3-{1-[5-(3,4-dihydro-1H-isoquinolin-2-yl)-5-oxopentan-1-yl]piperidin-4-yl}-1H-indole;

4-Chloro-3-{1-[6-(3,4-dihydro-1H-isoquinolin-2-yl)-6-oxohexan-1-yl]piperidin-4-yl}-1H-indole;

5-Fluoro-3-{1-[5-(3,4-dihydro-1H-isoquinolin-2-yl)-5-oxopentan-1-yl]piperidin-4-yl}-1H-indole;

5-Fluoro-3-{1-[6-(3,4-dihydro-1H-isoquinolin-2-yl)-6-oxohexan-1-yl]piperidin-4-yl}-6-Chloro-3-{1-[3-(3,4-dihydro-1H-isoquinolin-2-yl)-3-oxopropan-1-yl]piperidin-4-yl}-1H-indole;

6-Chloro-3-{1-[6-(3,4-dihydro-1H-isoquinolin-2-yl)-6-oxohexan-1-yl]piperidin-4-yl}-1H-indole;

7-Chloro-3-{1-[4-(3,4-dihydro-1H-isoquinolin-2-yl)-4-oxobutan-1-yl]piperidin-4-yl}-1H-indole;

7-Chloro-3-{1-[5-(3,4-dihydro-1H-isoquinolin-2-yl)-5-oxopentan-1-yl]piperidin-4-yl}-1H-indole;

7-Chloro-3-{1-[6-(3,4-dihydro-1H-isoquinolin-2-yl)-6-oxohexan-1-yl]piperidin-4-yl}-1H-indole;

4-Fluoro-3-{1-[3-(3,4-dihydro-2H-quinolin-1-yl)-3-oxopropan-1-yl]piperidin-4-yl}-1H-indole;

4-Fluoro-3-{1-[4-(3,4-dihydro-2H-quinolin-1-yl)-4-oxobutan-1-yl]piperidin-4-yl}-1H-indole;

4-Chloro-3-{1-[3-(3,4-dihydro-2H-quinolin-1-yl)-3-oxopropan-1-yl]piperidin-4-yl}-1H-indole;

4-Chloro-3-{1-[4-(3,4-dihydro-2H-quinolin-1-yl)-4-oxobutan-1-yl]piperidin-4-yl}-1H-indole;

5-Fluoro-3-{1-[3-(3,4-dihydro-2H-quinolin-1-yl)-3-oxopropan-1-yl]piperidin-4-yl}-1H-indole;

5-Fluoro-3-{1-[4-(3,4-dihydro-2H-quinolin-1-yl)-4-oxobutan-1-yl]piperidin-4-yl}-1H-indole;

5-Fluoro-3-{1-[5-(3,4-dihydro-2H-quinolin-1-yl)-5-oxopentan-1-yl]piperidin-4-yl}-1H-indole;

5-Fluoro-3-{1-[6-(3,4-dihydro-2H-quinolin-1-yl)-6-oxohexan-1-yl]piperidin-4-yl}-1H-indole;

6-Chloro-3-{1-[3-(3,4-dihydro-2H-quinolin-1-yl)-3-oxopropan-1-yl]piperidin-4-yl}-1H-indole;

6-Chloro-3-{1-[6-(3,4-dihydro-2H-quinolin-1-yl)-6-oxohexan-1-yl]piperidin-4-yl}-1H-indole;

7-Chloro-3-{1-[4-(3,4-dihydro-2H-quinolin-1-yl)-4-oxobutan-1-yl]piperidin-4-yl}-1H-indole;

7-Chloro-3-{1-[5-(3,4-dihydro-2H-quinolin-1-yl)-5-oxopentan-1-yl]piperidin-4-yl}-1H-indole;

7-Chloro-3-{1-[6-(3,4-dihydro-2H-quinolin-1-yl)-6-oxohexan-1-yl]piperidin-4-yl}-1H-indole;

5-Fluoro-3-{1-[4-(3,4-dihydro-1H-isoquinolin-2-yl)butan-1-yl]piperidin-4-yl}-1H-indole; and 5-Fluoro-3-{1-[4-(6,7-dimethoxy-3,4-dihydro-1H-isoquinolin-2-yl)butan-1-yl]piperidin-4-yl}-1H-indole or pharmaceutically acceptable salts thereof.

23. A pharmaceutical composition comprising a compound of claim 1 in a therapeutically effective amount together with one or more pharmaceutically acceptable carriers or diluents.

24. A method of treating a CNS disorder selected from the group consisting of psychoses, anxiety disorders, depression, aggression, side effects induced by conventional antipsychotic agents, migraine, cognitive disorders, ADHD and the improvement of sleep comprising a administering to a patient in need thereof a therapeutically effective amount of a compound of claim 1.

25. The method of claim 24, wherein said psychosis is the positive and negative symptoms of schizophrenia.

26. The method of claim 24, wherein said anxiety disorders are selected from the group consisting of generalised anxiety disorder, panic disorder and obsessive compulsive disorder.

* * * * *